US007262012B2

(12) United States Patent
Furebring et al.

(10) Patent No.: US 7,262,012 B2
(45) Date of Patent: *Aug. 28, 2007

(54) METHOD FOR IN VITRO MOLECULAR EVOLUTION OF PROTEIN FUNCTION USING VARIED EXONUCLEASE DIGESTION IN TWO POLYNUCLEOTIDE POPULATIONS

(75) Inventors: Christina Furebring, Lund (SE); Roland Carlsson, Lund (SE); Carl Arne Krister Borrebaeck, Hjärup (SE); Ann-Christin Malmborg Hager, Helsingborg (SE)

(73) Assignee: Alligator Bioscience AB, Lund (SE)

( * ) Notice: Subject to any disclaimer, the term of this patent is extended or adjusted under 35 U.S.C. 154(b) by 88 days.

This patent is subject to a terminal disclaimer.

(21) Appl. No.: 10/514,399

(22) PCT Filed: May 16, 2003

(86) PCT No.: PCT/GB03/02102

§ 371 (c)(1),
(2), (4) Date: Nov. 15, 2004

(87) PCT Pub. No.: WO03/097834

PCT Pub. Date: Nov. 27, 2003

(65) Prior Publication Data

US 2006/0166198 A1   Jul. 27, 2006

Related U.S. Application Data

(63) Continuation-in-part of application No. 10/321,195, filed on Dec. 17, 2002, now Pat. No. 7,153,655.

(30) Foreign Application Priority Data

May 17, 2002 (GB) .................................. 0211369.4

(51) Int. Cl.
C12Q 1/68 (2006.01)
C12P 19/34 (2006.01)
(52) U.S. Cl. .................... 435/6; 435/91.1; 435/91.2
(58) Field of Classification Search ............... 435/6, 435/91.1, 91.2
See application file for complete search history.

(56) References Cited

U.S. PATENT DOCUMENTS

| 4,683,202 | A | 7/1987 | Mullis |
| 4,888,286 | A | 12/1989 | Crea |
| 4,994,368 | A | 2/1991 | Goodman et al. |
| 5,023,171 | A | 6/1991 | Ho et al. |
| 5,043,272 | A | 8/1991 | Hartley |
| 5,223,408 | A | 6/1993 | Goeddel et al. |
| 5,252,479 | A | 10/1993 | Srivastava |
| 5,270,170 | A | 12/1993 | Schatz et al. |
| 5,338,665 | A | 8/1994 | Schatz et al. |
| 5,491,074 | A | 2/1996 | Aldwin et al. |
| 5,498,530 | A | 3/1996 | Schatz et al. |
| 5,512,463 | A | 4/1996 | Stemmer |
| 5,514,568 | A | 5/1996 | Stemmer |
| 5,521,291 | A | 5/1996 | Curiel et al. |
| 5,573,907 | A | 11/1996 | Carrino et al. |

(Continued)

FOREIGN PATENT DOCUMENTS

EP   0368684   5/1990

(Continued)

OTHER PUBLICATIONS

Henriquez and Gennaro, "A simple strategy to generate small deletions using Bal31 nuclease", *Nuc. Acids Res.*, 18(22):6735-6 (1990).

(Continued)

*Primary Examiner*—Kenneth R. Horlick
(74) *Attorney, Agent, or Firm*—Pabst Patent Group LLP

(57) ABSTRACT

A method for in vitro molecular evolution of protein function The invention provides a method for generating a polynucleotide sequence or population of sequences from parent single-stranded polynucleotide sequences encoding one or more protein motifs, comprising the steps of (a) providing a first population of single-stranded polynucleotide molecules and a second population of single-stranded polynucleotide molecules, the first and second populations together constituting plus and minus strands of parent polynucleotide sequences, (b) carrying out a reaction for digesting the first and second populations of single-stranded polynucleotide molecules with an exonuclease to generate corresponding populations of single-stranded polynucleotide fragments, (c) contacting said fragments generated from the plus strands with fragments generated from the minus strands and optionally, adding primer sequences that anneal to the 3' and 5'ends of at least one of the parent polynucleotides under annealing conditions, and (d) amplifying the fragments that anneal to each other to generate at least one polynucleotide sequence encoding one or more protein motifs having altered characteristics as compared to the one or more protein motifs encoded by said parent polynucleotides, wherein, in step (b), at least one parameter of the reaction used for digestion of the first population of single-stranded polynucleotide molecules is different from the equivalent parameter(s) used in the reaction for digestion of the second population of single-stranded polynucleotide molecules. Preferably, the reaction parameter is selected from exonuclease type, exonuclease concentration, reaction volume, duration of the digestion reaction, temperature of the reaction mixture, pH of the reaction mixture, length of parent single-stranded polynucleotide sequences, amount of single-stranded polynucleotide molecules and buffer composition of the reaction mixture.

29 Claims, 26 Drawing Sheets

U.S. PATENT DOCUMENTS

| | | | |
|---|---|---|---|
| 5,605,793 | A | 2/1997 | Stemmer |
| 5,712,089 | A | 1/1998 | Borrebaeck et al. |
| 5,723,323 | A | 3/1998 | Kauffman et al. |
| 5,733,731 | A | 3/1998 | Schatz et al. |
| 5,733,753 | A | 3/1998 | Jorgensen |
| 5,763,192 | A | 6/1998 | Kauffman et al. |
| 5,798,208 | A | 8/1998 | Crea |
| 5,811,238 | A | 9/1998 | Stemmer et al. |
| 5,814,476 | A | 9/1998 | Kauffman et al. |
| 5,817,483 | A | 10/1998 | Kauffman et al. |
| 5,824,514 | A | 10/1998 | Kauffman et al. |
| 5,830,650 | A | 11/1998 | Crea |
| 5,830,696 | A | 11/1998 | Short |
| 5,830,721 | A | 11/1998 | Stemmer et al. |
| 5,834,252 | A | 11/1998 | Stemmer et al. |
| 5,837,458 | A | 11/1998 | Minshull et al. |
| 5,858,657 | A | 1/1999 | Winter et al. |
| 5,858,725 | A | 1/1999 | Crowe et al. |
| 5,871,907 | A | 2/1999 | Winter et al. |
| 5,925,544 | A | 7/1999 | Jorgensen |
| 5,928,905 | A | 7/1999 | Stemmer et al. |
| 5,939,250 | A | 8/1999 | Short |
| 5,965,408 | A | 10/1999 | Short |
| 5,969,108 | A | 10/1999 | McCafferty et al. |
| 5,976,862 | A | 11/1999 | Kauffman et al. |
| 6,096,548 | A | 8/2000 | Stemmer |
| 6,117,679 | A | 9/2000 | Stemmer |
| 6,132,970 | A | 10/2000 | Stemmer |
| 6,143,527 | A | 11/2000 | Pachuk et al. |
| 6,153,410 | A | 11/2000 | Arnold et al. |
| 6,156,511 | A | 12/2000 | Schatz et al. |
| 6,159,687 | A | 12/2000 | Vind |
| 6,159,688 | A | 12/2000 | Borchert et al. |
| 6,159,690 | A | 12/2000 | Borrebaeck et al. |
| 6,165,793 | A | 12/2000 | Stemmer |
| 6,171,820 | B1 | 1/2001 | Short |
| 6,177,263 | B1 | 1/2001 | Arnold et al. |
| 6,180,406 | B1 | 1/2001 | Stemmer |
| 6,238,884 | B1 | 5/2001 | Short et al. |
| 6,251,674 | B1 | 6/2001 | Tobin et al. |
| 6,265,201 | B1 | 7/2001 | Wackett et al. |
| 6,277,638 | B1 | 8/2001 | Stemmer |
| 6,287,861 | B1 | 9/2001 | Stemmer et al. |
| 6,287,862 | B1 | 9/2001 | delCardayre et al. |
| 6,291,165 | B1 | 9/2001 | Borchert et al. |
| 6,291,242 | B1 | 9/2001 | Stemmer |
| 6,291,650 | B1 | 9/2001 | Winter et al. |
| 6,297,053 | B1 | 10/2001 | Stemmer |
| 6,303,344 | B1 | 10/2001 | Patten et al. |
| 6,309,883 | B1 | 10/2001 | Minshull et al. |
| 6,319,713 | B1 | 11/2001 | Patten et al. |
| 6,319,714 | B1 | 11/2001 | Crameri et al. |
| 6,323,030 | B1 | 11/2001 | Stemmer |
| 6,326,204 | B1 | 12/2001 | delCardayre et al. |
| 6,326,206 | B1 | 12/2001 | Bjornvad et al. |
| 6,329,178 | B1 | 12/2001 | Patel et al. |
| 6,335,160 | B1 | 1/2002 | Patten et al. |
| 6,335,179 | B1 | 1/2002 | Short |
| 6,335,198 | B1 | 1/2002 | delCardayre et al. |
| 6,337,186 | B1 | 1/2002 | Krebber |
| 6,344,356 | B1 | 2/2002 | Stemmer |
| 6,352,842 | B1 | 3/2002 | Short |
| 6,352,859 | B1 | 3/2002 | delCardayer et al. |
| 6,355,484 | B1 | 3/2002 | Patten et al. |
| 6,358,709 | B1 | 3/2002 | Short et al. |
| 6,358,712 | B1 | 3/2002 | Jarrell et al. |
| 6,358,740 | B1 | 3/2002 | Patten et al. |
| 6,358,742 | B1 | 3/2002 | Stemmer |
| 6,361,974 | B1 | 3/2002 | Short et al. |
| 6,365,377 | B1 | 4/2002 | Patten et al. |
| 6,365,408 | B1 | 4/2002 | Stemmer |
| 6,368,798 | B1 | 4/2002 | Short |
| 6,368,805 | B1 | 4/2002 | Borchert et al. |
| 6,368,861 | B1 | 4/2002 | Crameri et al. |
| 6,372,497 | B1 | 4/2002 | Stemmer |
| 6,376,246 | B1 | 4/2002 | Crameri et al. |
| 6,379,964 | B1 | 4/2002 | delCardayre et al. |
| 6,387,702 | B1 | 5/2002 | Stemmer |
| 6,391,552 | B2 | 5/2002 | Stemmer |
| 6,391,640 | B1 | 5/2002 | Minshull et al. |
| 6,395,547 | B1 | 5/2002 | Stemmer |
| 6,399,383 | B1 | 6/2002 | Apt et al. |
| 6,406,855 | B1 | 6/2002 | Patten et al. |
| 6,406,910 | B1 | 6/2002 | Patten et al. |
| 6,413,745 | B1 | 7/2002 | Patten et al. |
| 6,413,774 | B1 | 7/2002 | Stemmer et al. |
| 6,420,175 | B1 | 7/2002 | Stemmer |
| 6,423,542 | B1 | 7/2002 | Crameri et al. |
| 6,426,224 | B1 | 7/2002 | Crameri et al. |
| 6,429,004 | B1 | 8/2002 | Murphy et al. |
| 6,436,675 | B1 | 8/2002 | Welch et al. |
| 6,440,668 | B1 | 8/2002 | Short |
| 6,444,426 | B1 | 9/2002 | Short et al. |
| 6,444,468 | B1 | 9/2002 | Stemmer et al. |
| 6,479,258 | B1 | 11/2002 | Short |
| 6,479,652 | B1 | 11/2002 | Crameri et al. |
| 6,482,647 | B1 | 11/2002 | Stemmer |
| 6,483,011 | B1 | 11/2002 | Stemmer et al. |
| 6,489,145 | B1 | 12/2002 | Short |
| 6,492,107 | B1 | 12/2002 | Kauffman et al. |
| 6,958,213 | B2 * | 10/2005 | Carlsson et al. ............... 435/6 |
| 2001/0006950 | A1 | 7/2001 | Punnonen et al. |
| 2001/0032342 | A1 | 10/2001 | Stemmer et al. |
| 2001/0039014 | A1 | 11/2001 | Bass et al. |
| 2001/0049104 | A1 | 12/2001 | Stemmer et al. |
| 2001/0049125 | A1 | 12/2001 | Stemmer et al. |
| 2002/0051976 | A1 | 5/2002 | Patten et al. |
| 2002/0058249 | A1 | 5/2002 | Subramanian et al. |
| 2002/0059659 | A1 | 5/2002 | Stemmer |

FOREIGN PATENT DOCUMENTS

| | | |
|---|---|---|
| EP | 0415731 | 3/1991 |
| EP | 0456304 | 11/1991 |
| EP | 0 557 897 | 9/1993 |
| EP | 0590689 | 4/1994 |
| FR | 2813314 | 3/2002 |
| GB | 9712512.4 | 6/1997 |
| WO | WO86/05803 | 10/1986 |
| WO | WO90/07936 | 7/1990 |
| WO | WO90/14430 | 11/1990 |
| WO | WO91/07506 | 5/1991 |
| WO | WO91/15581 | 10/1991 |
| WO | WO91/16427 | 10/1991 |
| WO | WO92/01047 | 1/1992 |
| WO | WO92/07075 | 4/1992 |
| WO | WO92/18645 | 10/1992 |
| WO | WO93/06213 | 4/1993 |
| WO | WO93/07282 | 4/1993 |
| WO | WO93/08278 | 4/1993 |
| WO | WO93/12257 | 6/1993 |
| WO | WO94/12632 | 6/1994 |
| WO | WO94/242313 | 10/1994 |
| WO | WO94/28173 | 12/1994 |
| WO | WO95/22625 | 8/1995 |
| WO | WO96/17056 | 6/1996 |
| WO | WO96/40750 | 12/1996 |
| WO | WO96/40987 | 12/1996 |
| WO | WO97/07205 | 2/1997 |
| WO | WO97/07206 | 2/1997 |
| WO | WO97/08320 | 3/1997 |
| WO | WO97/20078 | 6/1997 |
| WO | WO97/35957 | 10/1997 |
| WO | WO97/35966 | 10/1997 |

| | | |
|---|---|---|
| WO | WO98/01581 | 1/1998 |
| WO | WO98/05765 | 2/1998 |
| WO | WO98/13485 | 4/1998 |
| WO | WO98/13487 | 4/1998 |
| WO | WO98/25965 | 6/1998 |
| WO | WO98/27230 | 6/1998 |
| WO | WO98/28416 | 7/1998 |
| WO | WO98/31837 | 7/1998 |
| WO | WO98/32845 | 7/1998 |
| WO | WO98/41622 | 9/1998 |
| WO | WO98/41623 | 9/1998 |
| WO | WO98/41653 | 9/1998 |
| WO | WO98/42832 | 10/1998 |
| WO | WO98/58080 | 12/1998 |
| WO | WO99/21979 | 5/1999 |
| WO | WO99/23107 | 5/1999 |
| WO | WO99/23236 | 5/1999 |
| WO | WO99/33965 | 7/1999 |
| WO | WO99/41368 | 8/1999 |
| WO | WO99/41369 | 8/1999 |
| WO | WO99/41383 | 8/1999 |
| WO | WO99/41402 | 8/1999 |
| WO | WO99/45110 | 9/1999 |
| WO | WO99/57128 | 11/1999 |
| WO | WO99/58661 | 11/1999 |
| WO | WO99/65927 | 12/1999 |
| WO | WO 00/04190 | 1/2000 |
| WO | WO 00/09679 | 2/2000 |
| WO | WO 00/09727 | 2/2000 |
| WO | WO 00/12680 | 3/2000 |
| WO | WO 00/18906 | 4/2000 |
| WO | WO 00/20573 | 4/2000 |
| WO | WO 00/28008 | 5/2000 |
| WO | WO 00/28017 | 5/2000 |
| WO | WO 00/28018 | 5/2000 |
| WO | WO 00/34512 | 6/2000 |
| WO | WO 00/42560 | 6/2000 |
| WO | WO 00/42559 | 7/2000 |
| WO | WO 00/42561 | 7/2000 |
| WO | WO 00/46344 | 8/2000 |
| WO | WO 00/52155 | 9/2000 |
| WO | WO 00/53744 | 9/2000 |
| WO | WO 00/58517 | 10/2000 |
| WO | WO 00/61731 | 10/2000 |
| WO | WO 00/61740 | 10/2000 |
| WO | WO 00/72013 | 11/2000 |
| WO | WO 00/73433 | 12/2000 |
| WO | WO 00/77262 | 12/2000 |
| WO | WO 01/00234 | 1/2001 |
| WO | WO 01/02865 | 1/2001 |
| WO | WO 01/04287 | 1/2001 |
| WO | WO 01/12791 | 2/2001 |
| WO | WO 01/23401 | 4/2001 |
| WO | WO 01/25438 | 4/2001 |
| WO | WO 01/27306 | 4/2001 |
| WO | WO 01/32712 | 5/2001 |
| WO | WO 01/34835 | 5/2001 |
| WO | WO 01/38504 | 5/2001 |
| WO | WO 01/38513 | 5/2001 |
| WO | WO 01/42455 | 6/2001 |
| WO | WO 01/46476 | 6/2001 |
| WO | WO 01/51663 | 7/2001 |
| WO | WO 01/64864 | 9/2001 |
| WO | WO 01/64912 | 9/2001 |
| WO | WO 01/68803 | 9/2001 |
| WO | WO 01/70947 | 9/2001 |
| WO | WO 01/73000 | 10/2001 |
| WO | WO 01/75087 | 10/2001 |
| WO | WO 01/75158 | 10/2001 |
| WO | WO 01/75767 | 10/2001 |
| WO | WO 01/96551 | 12/2001 |
| WO | WO 02/04629 | 1/2002 |
| WO | WO 02/10358 | 2/2002 |
| WO | WO 02/10750 | 2/2002 |
| WO | WO 02/16606 | 2/2002 |
| WO | WO 02/22663 | 3/2002 |
| WO | WO 02/29032 | 4/2002 |
| WO | WO 02/29071 | 4/2002 |
| WO | WO 02/38757 | 5/2002 |
| WO | WO 02/48351 | 6/2002 |
| WO | WO92/15702 | 9/2002 |

OTHER PUBLICATIONS

Molecular Libraries retrieved from http://www.immun.lth.se/texter/project_mol-libraries.thml on Dec. 28, 2005.

Ostermeier, et al., "Combinatorial protein engineering by incremental truncation", *Proc Natl Acad Sci U S A.*, 96(7):3562-7 (1999).

Recombinant DNA in Molecular LABFAX, ed. T. A. Brown., Academic Press, San Diegao, California. p. 128, 129, and 138 (1998).

Sharrocks and Hornby, "A rapid method for Bal31 deletion analysis", *Nuc. Acids Res.*, 15(20):8564 (1987).

Arnold, et al. "Combinatorial and computational challenges for biocatalyst design", *Nature*, 409(6817):253-7 (2001).

Balint and Larrick, "Antibody engineering by parsimonious mutagenesis", *Gene*, 137(1):109-18 (1993).

Beaudry and Joyce, "Directed evolution of an RNA enzyme", *Science*, 257(5070):635-41 (1992).

Berger, et al., "Phoenix mutagenesis: one-step reassembly of multiply cleaved plasmids with mixtures of mutant and wild-type fragments", Anal Biochem., 214(2):571-9 (1993).

Berkhout and Klaver "In vivo selection of randomly mutated retroviral genomes", *Nucleic Acids Res.*, 21(22):5020-4 (1993).

Blakely, et al., "Hydrogen peroxide-induced base damage in deoxyribonucleic acid", *Radiat Res.*, 121(3):338-43 (1990).

Bourgaux, et al., "Preferred crossover sites on polyomavirus DNA", *J Virol.*, 64(5):2327-36 (1990).

Casorati, et al. "The T cell receptor alpha beta V-J shuffling shows lack of autonomy between the combining site and the constant domain of the receptor chains", *Eur J Immunol.*, 23(2):586-9 (1993).

Chambers Dictionary of Science and Technology, p. 995 (1999).

Clackson, et al. "Making antibody fragments using phage display libraries", *Nature*, 352(6336):624-8 (1991).

Crameri, et al., "Improved green fluorescent protein by molecular evolution using DNA shuffling", *Nat Biotechnol.*, 14(3):315-9 (1996).

Daugherty, et al., "Polymerase chain reaction facilitates the cloning, CDR-grafting, and rapid expression of a murine monoclonal antibody directed against the CD18 component of leukocyte integrins", *Nucleic Acids Res.*, 19(9):2471-6 (1991).

Demple and Linn, "5,6-saturated thymine lesions in DNA: production by ultraviolet light or hydrogen peroxide", *Nucleic Acids Res.*, 10:3781-9 (1989).

Dillon and Rosen, "A rapid method for the construction of synthetic genes using the polymerase chain reaction", *Biotechniques*, 9(3):298, 300 (1990).

Dimmock and Primrose, Introduction to Modern Virology, 3$^{rd}$ Ed., Blackwell Scientific Publications, 1987.

Feinberg and Vogelstein, "A technique for radiolabeling DNA restriction endonuclease fragments to high specific activity", *Anal Biochem.*, 132(1):6-13 (1983).

Filho and Meneghini, "In vivo formation of single-strand breaks in DNA by hydrogen peroxide is mediated by the Haber-Weiss reaction", *Biochim Biophys Acta.*, 781(1-2):56-63 (1984).

Frappier, et al., "Alternative homologous and nonhomologous products arising from intramolecular recombination", *J Virol.*, 64(10):5058-65 (1990).

Hall, "Toward an understanding of evolutionary potential", *FEMS Microbilogy Letts.*, 178:1-6 (1999).

Horton, et al., "Gene splicing by overlap extension: tailor-made genes using the polymerase chain reaction", *Biotechniques*, 8(5):528-35 (1990).

Horton, et al., "Gene splicing by overlap extension", *Methods Enzymol.*, 217:270-9 (1993).

Judo, et al., "Stimulation and suppression of PCR-mediated recombination", *Nucleic Acids Res.*, 26(7):1819-25 (1998).
Kauffman and Ellington, "Thinking combinatorially", *Curr Opin Chem Biol.*, 3(3):256-9 (1999).
Kaushansky, et al., "Structure-function relationships of interleukin-3. An analysis based on the function and binding characteristics of a series of interspecies chimera of gibbon and murine interleukin-3", *J Clin Invest.*, 90(5):1879-88 (1992).
Krishnan, et al., "Direct and crossover PCR amplification to facilitate Tn5supF-based sequencing of lambda phage clones", *Nucleic Acids Res.*, 19(22):6177-82 (1991).
Lassner and Bedrook, "Directed molecular evolution in plant improvement", *Curr Opin Plant Biol.*, 4(2):152-6 (2001).
Life: The Science of Biology. 3rd Edition, Sinauer Associates, p. 55 (1992).
Lewin, in *Genes III*, 3rd edition, John Wiley and Sons, New York, p. 722, (1987).
Lewin, in *Genes V*, 5th edition, Oxford University Press, p. 647 (1994).
Lowe, "Oligomeric and biogenetic combinatorial libraries", *Nat Prod Rep.*, 16(6):641-51 (1999).
Marks, et al., "By-passing immunization. Human antibodies from V-gene libraries displayed on phage", *J Mol Biol.*, 222(3):581-97 (1991).
Marton, et al., "DNA nicking favors PCR recombination", *Nucleic Acids Res.*, 19(9):2423-6 (1991).
McPherson, Directed Mutagenesis, Oxford Univ. Press, (1991).
Merz, et al., "Improving the catalytic activity of a thermophilic enzyme at low temperatures", *Biochemistry*, 39(5):880-9 (2000).
Molecular Cell Biology, 3rd Edition, W.H. freeman and Company, p. G-16 (1995).
Mouret, et al., "Ionic and radical oxidations of DNA by hydrogen peroxide", *Chem Biol Interact.*, 77(2):187-201 (1991).
Mullis, et al., "Specific enzymatic amplification of DNA in vitro: the polymerase chain reaction", *Cold Spring Harb Symp Quant Biol.*, IPt 1:263-73 (1986).
NCBI database entries (partial) for *Homo sapiens* insulin, myoglobin, L-selectin, rhodopsin kinase and complement component C3 mRNAs.
Near, "Gene conversion of immunoglobulin variable regions in mutagenesis cassettes by replacement PCR mutagenesis", *Biotechniques*, 12(1):88-97 (1992).
Ness, et al., "DNA shuffling of subgenomic sequences of subtilisin", *Nat Biotechnol.*, (9):893-6 (1999).
Ness, et al., "Molecular Breeding: The natural approach to protein design", *Advances in Protein Chemistry*, 55:261-92 (2001).
Orum, et al., "Efficient method for constructing comprehensive murine Fab antibody libraries displayed on phage", *Nucleic Acids Res.*, 21(19):4491-8 (1993).
Patten, et al., "Applications of DNA shuffling to pharmaceuticals and vaccines", *Curr Opin Biotechnol.*, 8(6):724-33 (1997).
Perlak, "Single step large scale site-directed in vitro mutagenesis using multiple oligonucleotides", *Nucleic Acids Res.*, 18(24):7457-8 (1990).
Povirk and Steighner, "Oxidized apurinic/apyrimidinic sites formed in DNA by oxidative mutagens", *Mutat Res.*, 214(1):13-22 (1989).
Powell, et al, "Breeding of retroviruses by DNA shuffling for improved stability and processing yields", *Nat Biotechnol.*, 18(12):1279-82 (2000).
Prodromou and Pearl, "Recursive PCR: a novel technique for total gene synthesis", *Protein Eng.*, 5(8):827-9 (1992).
Punnonen, "Molecular breeding of allergy vaccines and antiallergic cytokines", *Int Arch Allergy Immunol.*, 121(3):173-82 (2000).
Punnonen, et al., *Science and Medicine*, 121:38-47 (2000).
Rhaese and Freese, "Chemical analysis of DNA alterations. I. Base liberation and backbone breakage of DNA and oligodeoxyadenylic acid induced by hydrogen peroxide and hydroxylamine", *Biochim Biophys Acta.*, 155(2):476-90 (1968).
Sagripanti and Draemer, "Site-specific oxidative DNA damage at polyguanosines produced by copper plus hydrogen peroxide", *J. Biol. Chem.*, 264:1729-34 (1989).

Saiki, et al., "Primer-directed enzymatic amplification of DNA with a thermostable DNA polymerase", *Science*, 239(4839):487-91 (1988).
Sambrook, et al., in *Molecular Cloning.* A Laboratory Manual, 2nd edition, Cold Springs Harbor Laboratory Press, chapters 16-18 (1989).
Shi, et al., "Rapid PCR construction of a gene containing Lym-1 antibody variable regions", *PCR Methods Appl.*, 3(1):46-53 (1993).
Shuldiner, et al., "Hybrid DNA artifact from PCR of closely related target sequences", *Nucleic Acids Res.*, 17(11):4409 (1989).
Soong, et al., "Molecular breeding of viruses", *Nat Genet.*, 25(4):436-9 (2000).
Suzuki, An Introduction to Genetic Analysis, 4th Edition, W.H. Freeman and Company, p. 322 (1989).
Tobin, et al., "Directed evolution: the 'rational' basis for 'irrational' design", *Curr Opin Struct Biol.*, 10(4):421-7 (2000).
Weisberg, et al., "Simultaneous mutagenesis of multiple sites: application of the ligase chain reaction using PCR products instead of oligonucleotides", *Biotechniques*, 15(1):68-70, 72-4, 76 (1993).
Whalen, et al., "DNA shuffling and vaccines", *Curr Opin Mol Ther.*, 3(1):31-6 (2001).
Zaphiropoulos, "Non-homologous recombination mediated by *Thermus aquaticus* DNA polymerase I. Evidence supporting a copy choice mechanism", *Nucleic Acids Res.*, 26(12):2843-8 (1998).
Zoller, "New recombinant DNA methodology for protein engineering", *Curr Opin Biotechnol.*, 3(4):348-54 (1992).
Alber, et al., "Contributions of hydrogen bonds of Thr 157 to the thermodynamic stability of phage T4 lysozyme" *Nature* 330(6143):41-46 (1987).
Arrizubieta, et al., "Increased thermal resistance and modification of the catalytic properties of a beta-glucosidase by random mutagenesis and in vitro recombination" *J. Biol. Chem.* 275(37):28843-28848 (2000).
Barbas, et al., "Assembly of combinatorial antibody libraries on phage surfaces: The gene III site" *PNAS USA*, 88:7978-7982 (1991).
Barbas, et al., "Semisynthetic combinatorial antibody libraries: A chemical solution to the diversity problem" *PNAS USA* 89:4457-4461 (1992).
Berger, et al., "Expanding the potential of restriction endonucleases: Use of hapaxoterministic enzymes" *Anal. Biochem.* 222:1-8 (1994).
Boder and Wittrup, "Yeast surface display for screening combinatorial polypeptide libraries" *Nat. Biotechnol.* 15:553-557 (1997).
Boublik, et al., "Eukaryotic virus display: Engineering the major surface glycoprotein of the *Autographa californica* nuclear polyhedrosis virus (AcNPV) for the presentation of foreign proteins of the virus surface" *Biotechnol.* 13:1079-1084 (1995).
Brown, "Chapter 5: DNA and RNA modifying enzymes" in *Molecular Biology Labfax Vol. I: Recombinant DNA* (Brown, ed.), pp. 154., BIOS Scientific Publishers Ltd: Oxford, 1991.
Buchholz, et al., "In vivo selection of protease cleavage sites from retrovirus display libraries" *Nature Biotechnol.* 16:951-954 (1998).
Cadwell, et al., "Randomization of genes by PCR mutagenesis" *PCR Methods Appl.* 2:28-33 (1992).
Cadwell, et al., "Mutagenic PCR" *PCR Methods Appl.* 3:S136-S140 (1994).
Casson and Manser, "Evaluatio of loss and change of specificity resulting from random mutagenesis of an antibody $V_H$ region[1]" *J. Immunol.* 155:5647-5654 (1995).
Chalfie, et al., "Green fluorescent protein as a marker for gene expression" *Science* 263:802-805 (1994).
Chang, et al., "Evolution of a cytokine using DNA family shuffling" *Nature Biotech.*, 17:793-797 (1999).
Chen, et al., "Tuning the activity of an enzyme for unusual environments: Sequential random mutagenesis of subtilisin E for catalysis in dimethylformamide" *PNAS USA* 90:5618-5622 (1993).
Christians, et al., "Directed evolution of thymidine kinase for AZY phosphorylation using DNA family shuffling" *Nature Biotech.* 17:259-264 (1999).
Crameri, et al., "DNA shuffling of a family of genes from diverse species accelerates directed evolution" *Nature* 391(6664):288-291 (1998).
Crameri, et al., "Molecular evolution of an arsenate detoxification pathway by DNA shuffling" *Nat. Biotechnol.* 15:436-438 (1997).

Crameri, et al., "Combinatorial multiple cassette mutagenesis creates all the permutations of mutant and wild-type sequences" *Biotechniques*, 18:194-196 (1995).

Deng, et al., "Simultaneous randomization of antibody CDRs by a synthetic ligase chain reaction strategy" *Nucl. Acid Res.* 21:4418-4419 (1993).

Dower, et al., "High efficiency transformation of *E. coli* by high voltage electroporation" *Nucleic Acids Res.* 16:6127-6145 (1988).

Eckstein, "Exogenous application of ribozymes for inhibiting gene expression" *Ciba found. Symp.* 209:207-216 (1997).

Engberg, et al., "Phage-display libraries of murine and human antibody Fab fragments" *Molecular Biotechnology*, 6:287-310 (1996).

Ernst, et al., "Baculovirus surface display: construction and screening of a eukaryotic epitope library" *Nucleic Acids Res.* 26:1718-1723 (1998).

Fisch, et al., "A strategy of exon shuffling for making large peptide repertoires displayed on filamentous bacteriophage" *PNAS USA* 93(15):7761-7766 (1996).

Gibbs, et al., "Degenerate oligonucleotide gene shuffling (DOGS): a method for enhancing the frequency of recombination with family shuffling" *Gene* 271:13-20 (2001).

Giver, et al., "Directed evolution of a thermostable esterase" *PNAS USA*, 89:12809-12813 (1998).

Gram, et al., "In vitro selection and affinity maturation of antibodies from a naïve combinatorial immunoglobulin library" *PNAS USA* 89:3576-3580 (1992).

Grabherr, et al., "Expression of foreign proteins on the surface of *Autographa californica* nuclear polyhedrosis virus" *Biotechniques* 22:730-735 (1997).

Granzerio, et al., "Baculovirus cDNA libraries for expression cloning of genes encoding cell-surface antigens" *J. Immunol. Meth.* 203:131-139 (1997).

Griffiths, et al., "Isolation of high affinity human antibodies directly from large synthetic repertoires" *EMBO J.* 13(14):3245-3260 (1994).

Hanahan, et al., "Studies on transformation of *Escherichia coli* with plasmids" *Mol. Biol.* 166:557-580 (1983).

Hansson, et al., "Evolution of differential substrate specificities in Mu class gluthathione transferases probed by DNA shuffling" *J. Mol. Biol.* 287:265-276 (1999).

Henke and Bornscheuer, "Directed evolution of an esterase from *Pseudomonas fluorescens*. Random mutagenesis by error-prone PCR or a mutator strain and identification of mutants showing enhanced enantioselectivity by a resorufin-based fluorescence assay" *Biol. Chem.* 308:1029-1033 (1999).

Higuchi, et al., "Cell display library for gene cloning of variable regions of human antibodies to hepatitis B surface antigen" *J. Immunol. Meth.* 202:193-204 (1997).

Ho, et al., "Site-directed mutagenesis by overlap extension using the polymerase chain reaction" *Gene* 77:51-59 (1989).

Hoogenboom, et al., "Human antibodies from synthetic repertoires of germline $V_H$ gene segments rearranged in vitro" *J. Mol. Biol.* 227:381-388 (1992).

Horton, et al., "Engineering hybrid genes without the use of restriction enzymes: gene splicing by overlap extension" *Gene* 77:61-68 (1989).

Huse, et al., Generatio of a large combinatorial library of the immunoglobulin repertoire in phage lambda *Science* 246:1275-1281 (1989).

Jansen, et al., "Disruption of phase during PCR amplification and cloning of heterozygous target sequences" *Nucleic Acids Res.* 18:5153-5156 (1990).

Joern, et al., "Analysis of shuffled gene libraries" *J. Mol. Biol.* 316:643-656 (2002).

Kikuchi, et al., "Novel family shuffling methods for the in vitro evolution of enzymes" *Gene*, 236:159-167 (1999).

Kikuchi, et al., "An effective family shuffling method using single-stranded DNA" *Gene* 243:133-137 (2000).

Kim, et al., "Bacterial cell surface display of an enzyme library for selective screening of improved cellulose variants" *Appl. Environ. Microbiol.* 66:788-793 (2000).

Kobayashi, et al., "Analysis of assembly fo synthetic antibody fragments: Expression of functional scFv with predefined specificity" *Biotechniques* 23:500-503 (1997).

Kong, et al., "Directed evolution of alpha-aspartyl dipeptidase form *Salmonella typhimurium*" *Biochemical and Biophysical Research Commun.* 289:137-142 (2001).

Kuipers, et al., "Improved site-directed mutagenesis method using PCR" *Nucleic Acids Res.* 19:4558 (1991).

Kwekkeboom, et al., "CD40 plays an essential role in the activation of human B cells by murine EL4B5 cells" *Immunol.* 79:439-444 (1993).

Larrick, et al., "Rapid cloning of rearranged immunoglobulin genes from human hybridoma cells using mixed primers and the polymerase chain reaction" *Biochem. Biophys. Res. Commun.* 160:1250-1256 (1989).

Leung, et al., "A method for random mutagenesis of a defined DNA segment using a modified polymerase chain reaction" *Technique* 1:11-15 (1989).

Lewin, *Genes IV*, pp. 272, Oxford University Press: Oxford, 1990.

Lewis and Crowe, "Immunoglobulin complementarity-determining region grafting by recombinant polymerase chain reaction to generate humanized monoclonal antibodies" *Gene* 101:297-302 (1991).

Liu, et al., "Replacement and deletion mutations in the catalytic domain and belt region of *Aspergillus awamori* glucoamylase to enhance thermostability" *Protein Eng.* 13:655-659 (2000).

Lu and Gray, "Kinetics and mechanism of BAL 31 nuclease action on small substrates and single-stranded DNA" *Biochimica et Biophysica Acta* 1251:125-138 (1995).

Luqmani and Lymboura, "Subtraction hybridization cloning of RNA amplified from different cell populations microdissected from cryostat tissue selections" *Anal. Biochem.* 222:102-109 (1994).

Lutz, et al., "Rapid generation of incremental truncation libraries for protein engineering using alpha-phosphothioate nucleotides" *Nucleic Acids Res.* 29:E16 (2001).

Marks, et al., "By-passing immunization: building high affinity human antibodies by chain shuffling" *Biotechnology* 10:779-783 (1992).

May, et al., "Inverting enantioselectivity by directed evolution of hydantoinase for improved production fo L-methionine" *Nat. Biotechnol.* 18:317-320 (2000).

McCafferty, et al., "Phage antibodies: filamentous phage displaying antibody variable domains" *Nature* 348:552-554 (1990).

Meyerhans, et al., "DNA recombination during PCR" *Nucl. Acids Res.* 18:1687-1691 (1990).

Moore, et al., "Directed evolution of a para-nitrobenzyl esterase for aqueous-organic solvents" *Nature Biotechnology* 14:458-467 (1996).

Mottershead, et al., "Baculoviral display of the green fluorescent protein and rubella virus envelope proteins" *Biochem. Biophys. Res. Com.* 238:717-722 (1997).

Orlandi, et al., "Cloning immunoglobulin variable domains for expression by the polymerase chain reaction" *PNAS USA* 86:3833-3837 (1989).

Ostermeier, et al., "A combinatorial approach to hybrid enzymes independent of DNA homology" *Nat. Biotechnol.* 17:1205-1209 (1999).

Paabo, et al., "Ancient DNA and the polymerase chain reaction" *J. Biol. Chem.* 264:9709-9712 (1989).

Paabo, et al., "DNA damage promotes jumping between templates during enzymatic amplification" *J. Biol. Chem.* 265:4718-4721 (1990).

Parmely, et al., "Antibody-selectable filamentous fd phage vectors: affinity purification of target genes" *Gene* 73:305-318 (1988).

Pelletier, et al., "A RACHITT for our toolbox" *Nat. Biotechnol.*, 19:314-315 (2001).

Prickett, et al., "A calcium-dependent antibody for identification and purification of recombinant proteins" *Biotechniques* 7:580-589 (1987).

Roberts, et al., "Generation of an antibody with enhanced affinity and specificity for its antigen by protein engineering" *Nature* 328:731-734 (1987).

Schier, et al., "Isolation of picomolar affinity anti-c-erbB-2 single-chain Fv by molecular evolution of the complementarity determining regions in the center of the antibody binding site" *J. Mol. Biol.* 263(4):551-567 (1996).

Schmidt, et al., "Exonuclease digestion of chromosomes for in situ hybridization" *Nucleic Acids Res.* 16:10381 (1988).

Schmidt-Dannert, et al., "Molecular breeding of carotenoid biosynthetic pathways" *Nat. Biotechnol.* 18:750-753 (2000).

Sharrocks and Hornby, "A rapid method for Bal31 deletion analysis" *Nucleic Acids Res.* 15:8564 (1987).

Shyur, et al., "Site-directed mutagenesis of residues at subunit interfaces of porcine fructose-1,6-bisphosphatase" *J. Biol. Chem.* 271:3005-3010 (1996).

Sock, et al., "DNA replication of human polyomavirus JC is stimulated by NF-I in vivo" *Virology* 192:298-308 (1991).

Soderlind, et al., "Domain libraries: Synthetic diversity for de novo design of antibody V-regions" *Gene* 160:269-272 (1995).

Song, et al., "Simultaneous enhancement of thermostability and catalytic activity of phospholipase $A_1$ by evolutionary molecular engineering" *Appl. Environ. Microbiol.* 66:890-894 (2000).

Stemmer, "DNA shuffling by random fragmentation and reassembly: In vitro recombination for molecular evolution" *PNAS USA* 91:10747-10751 (1994).

Stemmer, "Rapid evolution of a protein in vitro by DNA shuffling" *Nature* 370:389-391 (1994).

Vaish, et al., "In vitro selection of a purine nucleotide-specific hammerhead-like ribozyme" *PNAS USA* 95(5):2158-2162 (1998).

Volkov, et al., "Methods for in vitro DNA recombination and random chimeragenesis" *Methods Enzymol.* 328:447-457 (2000).

Wan, et al., "In vitro evolution of horse heart myoglobin to increase peroxidase activity" *PNAS USA* 95:12825-12831 (1998).

Warren,e t al., "A rapid screen of active site mutants in glycinamide ribonucleotide transformylase" *Biochemistry* 35(27):8855-8862 (1996).

Yang, et al., "CDR walking mutagenesis for the affinity maturation of a potent human anti-HIV-a antibody into the picomolar range" *J. Mol. Biol.* 254:392-403 (1995).

Zhang, et al., "Directed evolution of a fucosidase from a galactosidase by DNA shuffling and screening" *PNAS USA* 94(9):4504-4509 (1997).

Zhao and Arnold, "Directed evolution converts subtilisin E into a functional equivalent of thermitase" *Protein Eng.* 12:47-53 (1999).

Zhao, et al., "Molecular evolution by staggered extension process (StEP) in vitro recombination" *Nat. Biotechnol.* 16:258-261 (1998).

\* cited by examiner

FIGURE 12

FIGURE 13
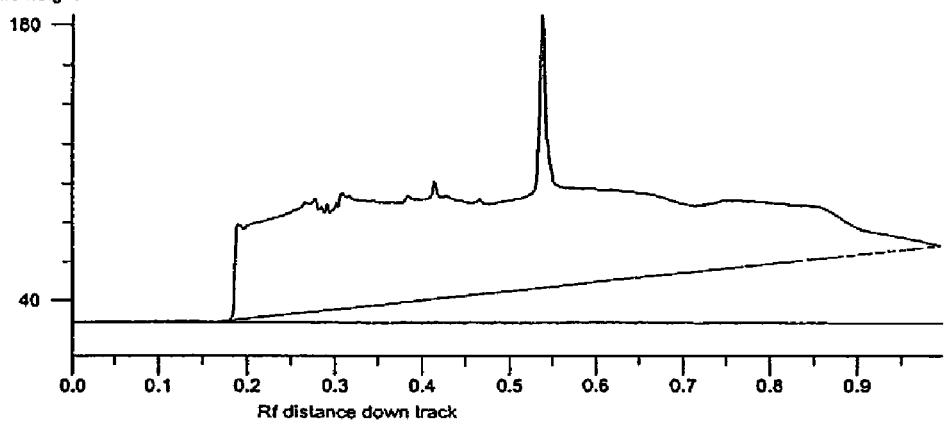
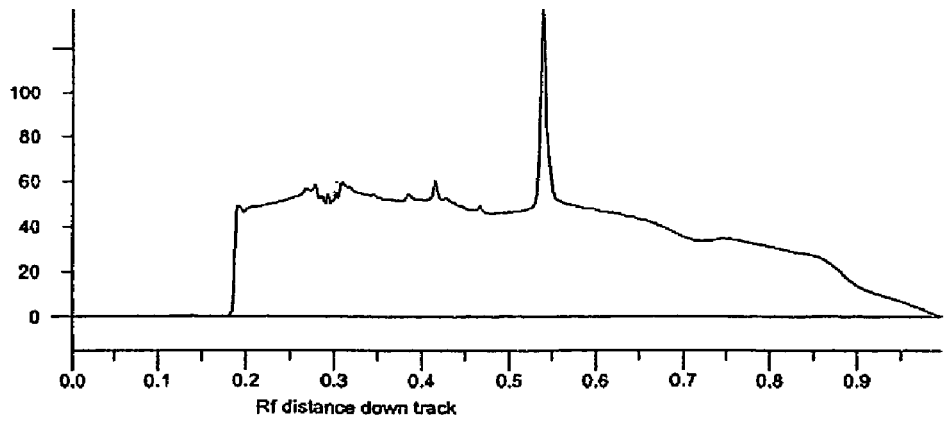

SEQUENCE LISTING

<160> NUMBER OF SEQ ID NOS: 8

<210> SEQ ID NO 1
<211> LENGTH: 44
<212> TYPE: DNA
<213> ORGANISM: Artificial Sequence

```
<220> FEATURE:
<223> OTHER INFORMATION: 1736 SfiI forward primer

<400> SEQUENCE: 1
aatactcgcg gcccagccgg ccatggccca caggtcaagc tcga                44

<210> SEQ ID NO 2
<211> LENGTH: 35
<212> TYPE: DNA
<213> ORGANISM: Artificial Sequence
<220> FEATURE:
<223> OTHER INFORMATION: 1735 NotI reversed primer

<400> SEQUENCE: 2
ttagagcctg cggccgcctt gtcatcgtcg tcctt                          35

<210> SEQ ID NO 3
<211> LENGTH: 44
<212> TYPE: DNA
<213> ORGANISM: Artificial Sequence
<220> FEATURE:
<223> OTHER INFORMATION: 1664 SfiI forward primer

<400> SEQUENCE: 3
attactcgcg gcccagccgg ccatggccca caggtcaagc tcga                44

<210> SEQ ID NO 4
<211> LENGTH: 35
<212> TYPE: DNA
<213> ORGANISM: Artificial Sequence
<220> FEATURE:
<223> OTHER INFORMATION: 1635 NotI reversed primer

<400> SEQUENCE: 4
ttagagcctg cggccgcctt gtcatcgtcg tcctt                          35

<210> SEQ ID NO 5
<211> LENGTH: 59
<212> TYPE: DNA
<213> ORGANISM: Artificial Sequence
<220> FEATURE:
<223> OTHER INFORMATION: pBR322 NheI forward stop primer

<400> SEQUENCE: 5
cactatggcg tgctgctagc gctatatgcg ttgatgcaat ttctatgagc acccgttct   59

<210> SEQ ID NO 6
<211> LENGTH: 38
<212> TYPE: DNA
<213> ORGANISM: Artificial Sequence
<220> FEATURE:
<223> OTHER INFORMATION: pBR322 EagI reversed primer

<400> SEQUENCE: 6
cgtagcccag cgcgtcggcc gccatgccgg cgataatg                       38

<210> SEQ ID NO 7
<211> LENGTH: 37
<212> TYPE: DNA
<213> ORGANISM: Artificial Sequence
<220> FEATURE:
<223> OTHER INFORMATION: pBR322 HindIII forward primer

<400> SEQUENCE: 7
cagcttatca tcgataagct ttaatgcggt agtttat                        37
```

```
<210> SEQ ID NO 8
<211> LENGTH: 65
<212> TYPE: DNA
<213> ORGANISM: pBR322 SalI reversed stop primer

<400> SEQUENCE: 8
tctcaagggc atcggtcgac gctctccctt atgcgactcc tgcattagga atcagcccag    60
tcgta                                                                65
```

METHOD FOR IN VITRO MOLECULAR EVOLUTION OF PROTEIN FUNCTION USING VARIED EXONUCLEASE DIGESTION IN TWO POLYNUCLEOTIDE POPULATIONS

CROSS-REFERENCE TO RELATED APPLICATIONS

This application is a 371 national phase entry of PCT/GB03/02102 filed on May 16, 2003, which claims priority to GB 0211369.4 filed on May 17, 2002; and this application is a continuation-in-part of U.S. patent application Ser. No. 10/321,195 filed on Dec. 17, 2002, now U.S. Pat. No. 7,153,655.

The present invention relates to a method for in vitro molecular evolution of protein function, in particular by shuffling of single-stranded DNA segments obtained using a nuclease.

Protein function can be modified and improved in vitro by a variety of methods, including site directed mutagenesis (Alber et al., Nature, 5; 330(6143):41-46, 1987) combinatorial cloning (Huse et al., Science, 246:1275-1281, 1989; Marks et al., Biotechnology, 10: 779-783, 1992) and random mutagenesis combined with appropriate selection systems (Barbas et al, PNAS. USA, 89: 4457-4461, 1992).

The method of random mutagenesis together with selection has been used in a number of cases to improve protein function and two different strategies exist. Firstly, randomisation of the entire gene sequence in combination with the selection of a variant (mutant) protein with the desired characteristics, followed by a new round of random mutagenesis and selection. This method can then be repeated until a protein variant is found which is considered optimal (Schier R. et al., J. Mol. Biol. 1996 263 (4): 551-567). Here, the traditional route to introduce mutations is by error prone PCR (Leung et al., Technique, 1: 11-15, 1989) with a mutation rate of approximately 0.7%. Secondly, defined regions of the gene can be mutagenised with degenerate primers, which allows for mutation rates up to 100% (Griffiths et al., EMBO. J, 13: 3245-3260, 1994; Yang et al., J. Mol. Biol. 254: 392-403, 1995). The higher the mutation rate used, the more limited the region of the gene that can be subjected to mutations.

Random mutation has been used extensively in the field of antibody engineering. In vivo formed antibody genes can be cloned in vitro (Larrick et al., Biochem. Biophys. Res. Commun. 160: 1250-1256, 1989) and random combinations of the genes encoding the variable heavy and light genes can be subjected to selection (Marks et al., Biotechnology, 10: 779-783, 1992). Functional antibody fragments selected can be further improved using random mutagenesis and additional rounds of selections (Schier R. et al., J. Mol. Biol. 1996 263 (4): 551-567).

The strategy of random mutagenesis is followed by selection. Variants with interesting characteristics can be selected and the mutated DNA regions from different variants, each with interesting characteristics, are combined into one coding sequence (Yang et al., J. Mol. Biol. 254: 392-403, 1995). This is a multi-step sequential process, and potential synergistic effects of different mutations in different regions can be lost, since they are not subjected to selection in combination. Thus, these two strategies do not include simultaneous mutagenesis of defined regions and selection of a combination of these regions.

Another process involves combinatorial pairing of genes which can be used to improve e.g. antibody affinity (Marks et al., Biotechnology, 10: 779-783, 1992). Here, the three CDR-regions in each variable gene are fixed and this technology does not allow for shuffling of individual gene segments in the gene for the variable domain, for example, including the CDR regions, between clones.

The concept of DNA shuffling (Stemmer, Nature 370: 389-391, 1994) utilises random fragmentation of DNA and assembly of fragments into a functional coding sequence. In this process, it is possible to introduce chemically synthesised DNA sequences and in this way target variation to defined places in the gene which DNA sequence is known (Crameri et al., Biotechniques, 18: 194-196, 1995). Stemmer and coworkers developed this in vitro method, which resembles the normal evolution process of protein in nature. The DNA shuffling generates diversity by recombination, combining useful mutations from individual genes. It has been used successfully for artificial evolution of different proteins, e.g. enzymes and cytokines (Chang et al. Nature Biotech. 17, 793-797, 1999; Zhang et al. Proc. Natl. Acad. Sci. USA 94, 4504-4509,1997; Christians et al. Nature Biotech. 17, 259-264, 1999). The genes are randomly fragmented using DNase I and then reassembled by recombination with each other. The starting material can be either a single gene (first randomly mutated using error-prone PCR) or naturally occurring homologous sequences (so-called family shuffling). DNase I hydrolyses DNA preferentially at sites adjacent to pyrimidine nucleotides, therefore it is a suitable choice for random fragmentation of DNA. However, the activity is dependent on Mg or Mn ions, Mg ions restrict the fragment size to 50 bp, while the Mn ions will give fragment sizes less than 50 bp. Therefore, in order to have all possible sizes for recombination the gene in question needs to be treated at least twice with DNase I in the presence of either of the two different ions, followed by removal of these very same ions.

In theory, it is possible to shuffle DNA between any clones. However, if the resulting shuffled gene is to be functional with respect to expression and activity, the clones to be shuffled have preferably to be related or even identical, with the exception of a low level of random mutations. DNA shuffling between genetically different clones will generally produce non-functional genes. However, it has been proven by the methodology of ITCHY that interspecies fusion libraries can be created between fragments of the E. coli and human glycinamide ribonucleotide transformylase genes, which have only 50% identity on the DNA level (Ostermeier et al., Nat Biotechnol 17, 1205-9, 1999).

A successful recombination of two different genes requires formation of hetero-duplex molecules. In some cases the family shuffling almost only form homo-duplexes resulting in a low frequency of recombination. This problem has been addressed by using DNase I-digested single-stranded DNA (Kikuchi et al. Gene 243,133-137 2000).

Single-stranded DNA can be obtained using methods known in the art. For example, biotinylated primers may be used in the PCR reactions in combination with e.g. Dynabeads (Dynal, Norway) or AffiniTip Streptavidin Capture Micro-columns (Genosys Biotechnologies Inc., The Woodlands, USA). Alternatively, single-stranded DNA can be obtained by utilising bacteriophage that are able to pack single-stranded DNA (Viruses and Related Entities in Modern Microbiology, Principles and Applications pp. 171-192, Ed. E. A. Birge, Wm. C. Brown Publishers 1992; Sambrook et al. Molecular Cloning, A laboratory manual $2^{nd}$ edition. Cold Spring Habor Laboratory Press, 1989). In addition, asymmetric PCR methods may be used (see Example 1).

Selection of enzymes with altered and improved properties is often based on the actual function of the enzyme. For example, increased thermostability of an enzyme can be selected for by incubating transformed colonies at temperatures that cause inactivation of wild type enzyme. In addition, improved β-glucosidase activity can be identified by using PNPG as the substrate (Arrizubieta et al J Biol Chem Jun. 27, 2000).

Selection of functional proteins from molecular libraries has been revolutionised by the development of the phage display technology (Parmley et al., Gene, 73: 305-391 1988; McCafferty et al., Nature, 348: 552-554, 1990; Barbas et al., PNAS. USA, 88: 7978-7982, 1991). Here, the phenotype (protein) is directly linked to its corresponding genotype (DNA) and this allows for direct cloning of the genetic material, which can then be subjected to further modifications in order to improve protein function. Phage display has been used to clone functional binders from a variety of molecular libraries with up to $10^{11}$ transformants in size (Griffiths et al., EMBO. J. 13: 3245-3260, 1994). Thus, phage display can be used to directly clone functional binders from molecular libraries, and can also be used to improve further the clones originally selected. Other types of viruses that have been used for surface expression of protein libraries and selections thereof are baculovirus (Boublik et al Biotechnol 13:1079-1084. 1995; Mottershead et al Biochem Biophys Res Com 238:717-722, 1997; Grabherr et al Biotechniques 22:730-735, 1997) and retrovirus (Buchholz et al Nature Biotechnol 16:951-954, 1998).

Selection of functional proteins from molecular libraries can also be performed by cell surface display. Also here, the phenotype is directly linked to its corresponding genotype. Bacterial cell surface display has been used for e.g. screening of improved variants of carboxymethyl cellulase (CM-Case) (Kim et al Appl Environ Microbiol 66:788-93, 2000). Other cells that can be used for this purpose are yeast cells (Boder and Wittrup Nat. Biotechnol 15:553-557, 1997), COS cells (Higuchi et al J Immunol Meth 202:193-204, 1997) and insect cells (Granzerio et al J Immunol Meth 203:131-139, 1997; Ernst et al Nucleic Acids Res 26:1718-1723, 1998).

Random combination of DNA from different mutated clones in combination with selection of desired function is a more efficient way to search through sequence space as compared to sequential selection and combination of selected clones.

The present invention seeks to provide improved methods for in vitro protein evolution. In particular, the invention aims to provide more efficient recombination and shuffling methods, which will give rise to more altered molecules and thereby improve the probability of finding molecules with desirable properties.

According to a first aspect of the present invention, there is provided a method for generating a polynucleotide sequence or population of sequences from parent single-stranded (ss) polynucleotide sequences encoding one or more protein motifs, comprising the steps of a) providing a first population of single-stranded polynucleotide molecules and a second population of single-stranded polynucleotide molecules, the first and second populations together constituting plus and minus strands of parent polynucleotide sequences;

b) carrying out a reaction for digesting the first and second populations of single-stranded polynucleotide molecules with an exonuclease to generate corresponding populations of single-stranded polynucleotide fragments;

c) contacting said fragments generated from the plus strands with fragments generated from the minus strands and optionally, adding primer sequences that anneal to the 3' and 5'ends of at least one of the parent polynucleotides under annealing conditions;

d) amplifying the fragments that anneal to each other to generate at least one polynucleotide sequence encoding one or more protein motifs having altered characteristics as compared to the one or more protein motifs encoded by said parent polynucleotides.

wherein, in step (b), at least one parameter of the reaction used for digestion of the first population of single-stranded polynucleotide molecules is different from the equivalent parameter(s) used in the reaction for digestion of the second population of single-stranded polynucleotide molecules.

Thus, the invention provides a method for generating a variant polynucleotide sequence or population of variants from parent single-stranded polynucleotide sequences.

The use of different parameters of the reaction used for digestion of the first and second populations of single-stranded polynucleotide molecules provides the advantage of increased variability in the variant polynucleotides produced by the method of the invention.

Preferably, the polynucleotide molecules of step (a) are DNA molecules.

By 'corresponding populations of single-stranded polynucleotide fragments' we mean the population of fragments produced by digestion of the first and second populations of single-stranded polynucleotide molecules with an exonuclease.

By 'equivalent parameter' we mean the same parameter used in the reaction for digestion of the other population of single-stranded polynucleotide molecules. For example, the exonuclease used for digestion of the first population of single-stranded polynucleotide molecules may differ from the exonuclease used for digestion of the second population of single-stranded polynucleotide molecules.

By 'exonuclease' we mean a polypeptide, e.g. enzyme or fragment thereof, having exonucleolytic activity. Preferably, the exonucleolytic activity of the polypeptide is greater than the endonucleolytic activity of the polypeptide. More preferably, the polypeptide has exonucleolytic activity but is substantially free of endonucleolytic activity.

Advantageously, the parameter of the digestion reaction which differs is selected from exonuclease type, exonuclease concentration, reaction volume, duration of the digestion reaction, temperature of the reaction mixture, pH of the reaction mixture, length of parent single-stranded polynucleotide sequences, amount of single-stranded polynucleotide molecules and buffer composition of the reaction mixture.

In a preferred embodiment of the method of the first aspect of the invention, the exonuclease used for digestion of the first population of single-stranded polynucleotide molecules is different from the exonuclease used for digestion of the second population of single-stranded polynucleotide molecules. Preferably, the exonuclease used for digestion of the first population of single-stranded polynucleotide molecules is a 3' exonuclease (i.e. which preferentially or exclusively removes nucleotides from 3' terminus of ss polynucleotides) and the exonuclease used for digestion of the second population of single-stranded polynucleotide molecules is a 5' exonuclease (i.e. which preferentially or exclusively removes nucleotides from 5' terminus of ss polynucleotides).

In a further embodiment of the method of the first aspect of the invention, the exonuclease concentration used for digestion of the first population of single-stranded polynucleotide molecules is different from the exonuclease concentration used for digestion of the second population of single-stranded polynucleotide molecules.

In a further embodiment of the method of the first aspect of the invention, the reaction volume used for digestion of the first population of single-stranded polynucleotide molecules is different from the reaction volume used for digestion of the second population of single-stranded polynucleotide molecules.

In a further embodiment of the method of the first aspect of the invention, the duration of the digestion reaction used for digestion of the first population of single-stranded polynucleotide molecules is different from the duration of the digestion reaction used for digestion of the second population of single-stranded polynucleotide molecules.

In a further embodiment of the method of the first aspect of the invention, the temperature of the reaction mixture used for digestion of the first population of single-stranded polynucleotide molecules is different from the temperature of the reaction mixture used for digestion of the second population of single-stranded polynucleotide molecules.

In a further embodiment of the method of the first aspect of the invention, the pH of the reaction mixture used for digestion of the first population of single-stranded polynucleotide molecules is different from the pH of the reaction mixture used for digestion of the second population of single-stranded polynucleotide molecules.

In a further embodiment of the method of the first aspect of the invention, the length of the polynucleotides in the first population of single-stranded polynucleotide molecules is different from the length of the polynucleotides in the second population of single-stranded polynucleotide molecules.

In a further embodiment of the method of the first aspect of the invention, the buffer composition of the reaction mixture used for digestion of the first population of single-stranded polynucleotide molecules is different from the buffer composition of the reaction mixture used for digestion of the second population of single-stranded polynucleotide molecules.

In a further embodiment of the method of the first aspect of the invention, the amount of single-stranded polynucleotide molecules in the first population of single-stranded polynucleotide molecules is different from the amount of single-stranded polynucleotide molecules in the second population of single-stranded polynucleotide molecules.

In a further embodiment of the method of the first aspect of the invention, the first population of single-stranded polynucleotide molecules constitutes the plus strands of parent polynucleotide sequences and the second population of single-stranded polynucleotide molecules constitutes the minus strands of parent polynucleotide sequences.

Conveniently, step c) further comprises adding primer sequences that anneal to the 3' and/or 5'ends of at least one of the parent polynucleotides under annealing conditions.

Thus, the invention provides a method of combining polynucleotide fragments to generate a polynucleotide sequence or population of sequences of desired characteristics, which method comprises the steps of:
  a) digesting a linear parent single-stranded polynucleotide encoding one or more protein motifs with a nuclease other than DNase I to generate a population of single-stranded fragments of varying lengths;
  b) assembling a polynucleotide sequence from the sequences derived from step (a).

Preferably the method further comprises the step of (c) expressing the resulting protein encoded by the assembled polynucleotide sequence and d) screening the protein for desired characteristics.

By controlling the parameters of the exonuclease digestion reaction, the size of the polynucleotide fragments may be controlled. Determining the lengths of the polynucleotide fragments in this way avoids the necessity of having to provide a further step such as purifying the fragments of desired length from a gel.

In order to generate a polynucleotide sequence of desired characteristics the parent polynucleotides encoding one or more protein motifs may be subjected to mutagenesis to create a plurality of differently mutated derivatives thereof. Likewise, a parent polynucleotide may be obtained already encoding a plurality of variant protein motifs of unknown sequence.

Random mutation can be accomplished by any conventional method as described above, but a suitable method is error-prone PCR.

It is preferable to use PCR technology to assemble the single-stranded polynucleotide fragments into a double-stranded (ds) polynucleotide sequence.

The polynucleotide sequence is preferably DNA although RNA may be used. For simplicity the term polynucleotide will now be used in the following text in relation to DNA but it will be appreciated that the present invention is applicable to both RNA and DNA.

Preferably, any exonuclease that digests polynucleotide from the 5' prime end to the 3' prime, from the 3' to the 5' end or from both the 3' and the 5' ends may be used. Examples of suitable exonucleases which may be used in accordance with the present invention include BAL 31, exonuclease I, exonuclease V, exonuclease VII, exonuclease T7 gene 6, bacteriophage lambda exonuclease and exonuclease Rec $J_f$.

Using BAL 31 nuclease in the DNA shuffling process of the invention provides a fast, easy and controllable system. This enzyme can give all sizes of gene fragments and the activity of the enzyme can be easily controlled by stopping the digestion at various time points. BAL 31 is predominately a 3' prime exonuclease that removes mononucleotides from both 3' termini of the two strands of a linear DNA. BAL 31 is also an endonuclease; thus the single-stranded DNA generated by the 3' prime exonuclease activity is degraded by the endonuclease. The 3' prime exonuclease activity of the enzyme works about 20-fold more efficiently than the endonuclease. The enzyme concentrations are therefore important for the obtained DNA fragments. High concentration of enzyme favours blunt-ended DNA whereas at low concentrations the single-stranded DNA termini may be very long. BAL 31 consists of two kinetically distinct forms of the enzyme, a fast (F) and a slow (S) form. The S form is a proteolytic degradation product of the F form. Furthermore, BAL 31 works asynchronously, generating a population of DNA molecules whose termini have been resected to various extents and whose single-stranded tails vary in length. Both forms also act on ssDNA in an exonucleolytic fashion in a highly processive manner. The direction of attack is from the 5' end, in contrast to the mode of digestion of duplex DNA. It has been suggested that the nuclease molecules initially are non-productively bound away from the 5'ends and undergo facilitated diffusion to yield productive (terminally bound) enzyme-substrate complexes (Lu T and Gray jr. HB Biochimica et Biophysica Acta 1995, vol. $^{1251}$, p 125-138). The enzyme uses $Ca^{2+}$ as a co-factor which can be bound in complex with EGTA (Ethylene Glycol bis (β-amino ethyl Ether) N,N,N',N'-tetra acetic acid). Linear DNA sequences are digested with BAL31 and the reaction stopped at different time points by the addition of EGTA.

The individual digested fragments are purified, mixed and reassembled with PCR technology. The assembled (reconstituted) gene may then be cloned into an expression vector for expressing the protein. The protein may then be analysed for improved characteristics.

The method of the present invention provides several advantages over known shuffling techniques, including increased rates of recombination, increased variability and control of fragment size.

The method of the present invention produces a set of progressively shortened DNA fragments for each time point a DNA sample is taken from the BAL31 treatment. The DNA samples may be collected and pooled together or, optionally, individual samples may be chosen and used in the method. Thus the present invention allows a selection of what DNA samples are to be used in the recombination system and thereby offers a further degree of control.

The method of the present invention may be carried out on any polynucleotide which codes for a particular product, for example any protein having binding or catalytic properties e.g. antibodies or parts of antibodies, enzymes or receptors. Furthermore, any polynucleotide that has a function that may be altered, such as catalytic RNA, may be shuffled in accordance with the present invention. It is preferable that the parent polynucleotide encoding one or more protein motif is at least 12 nucleotides in length, more preferably at least 20 nucleotides in length, even more preferably more than 50 nucleotides in length. Polynucleotides being at least 100 nucleotides in length or even at least 200 nucleotides in length may be used. Where parent polynucleotides are used that encode large proteins such as enzymes or antibodies, these may be many hundreds or thousands of bases in length. The present invention may be carried out on any size of parent polynucleotide.

The present invention also provides polynucleotide sequences generated by the method described above having desired characteristics. These sequences may be used for generating gene therapy vectors and replication-defective gene therapy constructs or vaccination vectors for DNA-based vaccinations. In addition, the polynucleotide sequences may be used as research tools.

The present invention also provides a polynucleotide library of sequences generated by the method described above from which a polynucleotide may be selected which encodes a protein having the desired characteristics. It is preferable that the polynucleotide library is a DNA or cDNA library.

The present inventions also provides proteins such as enzymes, antibodies, and receptors having characteristics different to that of the wild type produced by the method described above. These proteins may be used individually or within a pharmaceutically acceptable carrier as vaccines or medicaments for therapy, for example, as immunogens, antigens or otherwise in obtaining specific antibodies. They may also be used as research tools.

The desired characteristics of a polynucleotide generated by the present invention or a protein encoded by a polynucleotide generated by the present invention may be any variation or alteration in the normal activity of the wild type (parent) polynucleotide or the polypeptide, protein or protein motifs it encodes. For example, it may be desirable to reduce or increase the catalytic activity of an enzyme, or improve or reduce the binding specificity of an antibody. Furthermore, if the protein or polynucleotide is an immunogen, it may be desirable to reduce or increase its ability to obtain specific antibodies against it.

The parent polynucleotide preferably encodes one or more protein motifs. These are defined as regions or elements of polynucleotide sequence that encode a polypeptide (i.e. amino acid) sequence which has, or potentially has, characteristic protein function. For example, a protein motif may define a portion of a whole protein, such as an epitope, a cleavage site or a catalytic site etc. However, within the scope of the present invention, an expressed protein motif does not have to display activity, or be "correctly" folded.

Several searchable databases of protein motifs and potential protein motifs are available, such as MOTIF, PROSITE, SMART and BLOCKS (www.blocks.fhcrc.org).

It may be desirable to modify a protein so as to alter the conformation of certain epitopes, thereby improving its antigenicity and/or reducing cross-reactivity. For example, should such a protein be used as an antigen, the modification may reduce any cross-reaction of raised antibodies with similar proteins.

Although the term "enzyme" is used, this is to be interpreted as also including any polypeptide having enzyme-like activity, i.e. a catalytic function. For example, polypeptides being part of an enzyme may still possess catalytic function. Furthermore, proteins such as interferons and cytokines are included. Likewise, the term "antibody" should be construed as covering any binding substance having a binding domain with the required specificity. This includes antibody fragments, derivatives, functional equivalents and homologues of antibodies, including synthetic molecules and molecules whose shape mimics that of an antibody enabling it to bind an antigen or epitope. Examples of antibody fragments, capable of binding an antigen or other binding partner are Fab fragment consisting of the VL, VH, Cl and CH1 domains, the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

In order to obtain expression of the generated polynucleotide sequence, the sequence may be incorporated in a vector having control sequences operably linked to the polynucleotide sequence to control its expression.

The vectors may include other sequences such as promoters or enhancers to drive the expression of the inserted polynucleotide sequence, further polynucleotide sequences so that the protein encoded for by the polynucleotide is produced as a fusion and/or nucleic acid encoding secretion signals so that the protein produced in the host cell is secreted from the cell. The protein encoded for by the polynucleotide sequence can then be obtained by transforming the vectors into host cells in which the vector is functional, culturing the host cells so that the protein is produced and recovering the protein from the host cells or the surrounding medium. Prokaryotic and eukaryotic cells are used for this purpose in the art, including strains of *E. coli*, yeast, and eukaryotic cells such as COS or CHO cells. The choice of host cell can be used to control the properties of the protein expressed in those cells, e.g. controlling where the protein is deposited in the host cells or affecting properties such as its glycosylation.

The protein encoded by the polynucleotide sequence may be expressed by methods well known in the art. Conveniently, expression may be achieved by growing a host cell in culture, containing such a vector, under appropriate conditions which cause or allow expression of the protein.

Systems for cloning and expression of a protein in a variety of different host cells are well known. Suitable host cells include bacteria, eukaryotic cells such as mammalian and yeast, and baculovirus systems. Also, utilising the retrovirus system for cloning and expression is a good alternative, since this virus can be used together with a number of cell types. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 3rd edition, Sambrook and Russell, 2001, Cold Spring Harbor Laboratory Press. Many known techniques and protocols for manipulation of polynucleotide sequences, for example in preparation of polynucleotide constructs, mutagenesis, sequencing, introduction of DNA into cells and gene expression, and analysis of proteins, are described in detail in Current Protocols in Molecular Biology, Ausubel et al. eds., John Wiley & Sons, 1992.

The system can be used for the creation of DNA libraries comprising variable sequences which can be screened for the desired protein function in a number of ways. Enzyme function can be screened for with methods specific for the actual enzyme function e.g. CMCase activity, β-glucosidase activity and also thermostability. Furthermore, phage display and cell surface display may be used for screening for enzyme function (Crameri A. et al., Nature 1998 15; 391 (6664):288-291; Zhang J. H. et al., PNAS. USA 1997 94 (9): 4504-4509; Warren M. S. et al., Biochemistry 1996, 9; 35(27): 8855-8862; Kim et al., Appl Environ Microbiol 66:788-93, 2000) as well as for altered binding properties of e.g. antibodies (Griffith et al., EMBO J. 113: 3245-3260, 1994).

A protein provided by the present invention may be used in screening for molecules which affect or modulate its activity or function. Such molecules may be useful in a therapeutic (possibly including prophylactic) context.

The present invention also provides vectors comprising polynucleotide sequences generated by the method described above.

The present inventions also provides compositions comprising either polynucleotide sequences, vectors comprising the polynucleotide sequences or proteins generated by the method described above and a pharmaceutically acceptable carrier or a carrier suitable for research purposes.

The present invention further provides a method comprising, following the identification of the polynucleotide or polypeptide having desired characteristics by the method described above, the manufacture of that polypeptide or polynucleotide in whole or in part, optionally in conjunction with additional polypeptides or polynucleotides.

Thus, a further aspect of the invention provides a method for making a polypeptide having desired properties, the method comprising the following steps:
(a) generating variant forms of a parent polynucleotide using a method according to the first aspect of the invention;
(b) expressing the variant polynucleotides produced in step (a) to produce variant polypeptides;
(c) screening the variant polypeptides for desired properties; and
(d) selecting a polypeptide having desired properties from the variant polypeptides.

The invention further provides a polypeptide obtained by the above method.

Following the identification of a polynucleotide or polypeptide having desired characteristics, these can then be manufactured to provide greater numbers by well-known techniques such as PCR, cloning and expression within a host cell.

The resulting polypeptides or polynucleotides may be used in the preparation of industrial enzymes, e.g. laundry detergent enzymes where an increased activity is preferred at lower temperatures. Alternatively, the manufactured polynucleotide or polypeptide may be used as a research tool, i.e. antibodies may be used in immunoassays, and polynucleotides may be used as hybridization probes or primers. Alternatively, the resulting polypeptides or polynucleotides may be used in the preparation of medicaments for diagnostic use, pharmaceutical use, therapy etc. as discussed as follows.

The polypeptides or polynucleotides generated by the methods of the invention and identified as having desirable characteristics can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Thus, the invention further provides a polypeptide produced by the methods of the invention for use in medicine and the use of provides a polypeptide produced by the methods of the invention in the preparation of a medicament for use in the treatment, therapy and/or diagnosis of a disease. Whether it is a polypeptide, e.g. an antibody or fragment thereof, an enzyme, a polynucleotide or nucleic acid molecule, identified following generation by the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique i.e. the activating agent, e.g. an enzyme, is produced in a vector by expression from encoding DNA in a viral vector). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated.

As a further alternative, the polynucleotide identified as having desirable characteristics following generation by the method of the present invention could be used in a method of gene therapy, to treat a patient who is unable to synthesize the active polypeptide encoded by the polynucleotide or unable to synthesize it at the normal level, thereby providing the effect provided by the corresponding wild-type protein.

Vectors such as viral vectors have been used in the prior art to introduce polynucleotides into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpes viruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding a polypeptide, or an active portion thereof, is to increase the amount of the expression product of the nucleic acid in cells in which the level of the wild-type polypeptide is absent or present only at reduced levels. Such treatment may be therapeutic in the treatment of cells which are already cancerous or prophylactic in the treatment of individuals known through screening to have a susceptibility allele and hence a predisposition to, for example, cancer.

The present invention also provides a kit for generating a polynucleotide sequence or population of sequences of desired characteristics comprising reagents for ssDNA preparation, an exonuclease and components for carrying out a PCR technique, for example, thermostable DNA (nucleotides) and a stopping device, for example, EGTA.

As outlined above the present invention conveniently provides for the creation of mutated enzyme gene sequences and their random combination to functional enzymes having desirable characteristics. As an example of this aspect of the invention, the enzyme genes are mutated by error prone PCR which results in a mutation rate of approximately 0.7%. The resulting pool of mutated enzyme genes are then digested with an exonuclease, e.g. BAL31, and the reaction inhibited by the addition of EGTA or by heat inactivation at different time points, resulting in a set of DNA fragments of different sizes. These may then be subjected to PCR based reassembly as described above. The resulting reassembled DNA fragments are then cloned and a gene library constructed. Clones may then be selected from this library and sequenced.

A further application of this technology is the generation of a population of variable DNA sequences which can be used for further selections and analyses. Besides encoding larger proteins, e.g. antibody fragments and enzymes, the DNA may encode peptides where the molecules functional characteristics can be used for the design of different selection systems. Selection of recombined DNA sequences encoding peptides has previously been described (Fisch et al., PNAS. USA 1996 Jul. 23; 93 (15): 7761-7766).

In addition, the variable DNA population can be used to produce a population of RNA molecules with e.g. catalytic activities. Vaish et al., (PNAS. USA 1998 Mar. 3; 95 (5): 2158-2162) demonstrated the design of functional systems for the selection of catalytic RNA and Eckstein F (Ciba Found. Symp. 1997; 209; 207-212) has outlined the applications of catalytic RNA by the specific introduction of catalytic RNA in cells. The system may be used to further search through the sequence space in the selection of functional peptides/molecules with catalytic activities based on recombined DNA sequences.

Aspects and embodiments of the present invention will now be illustrated, by way of example, with reference to the accompanying figures. Further aspects and embodiments will be apparent to those skilled in the art.

BRIEF DESCRIPTION OF THE DRAWINGS

FIG. 12 shows the gel chromatograms for lane 4.

FIG. 13 shows the gel chromatograms for lane 3.

EXAMPLES

Figure 1:
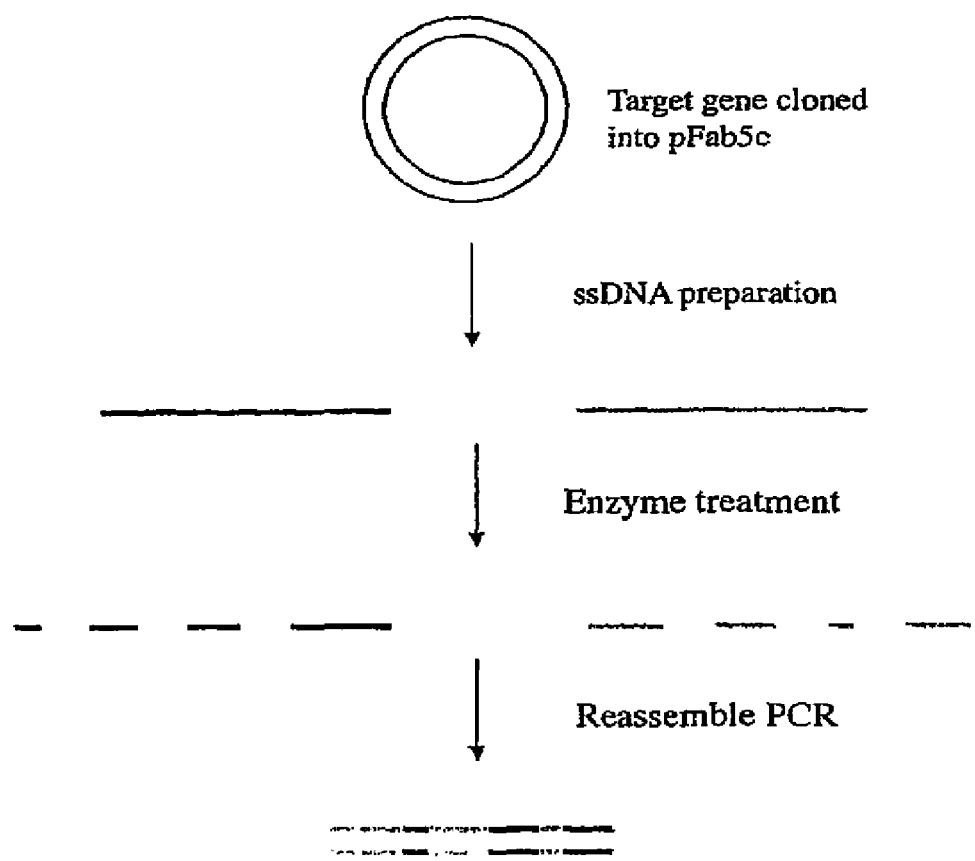
FIG. 1 shows the principle of the method from template molecule to improved molecule.
Figure 2:
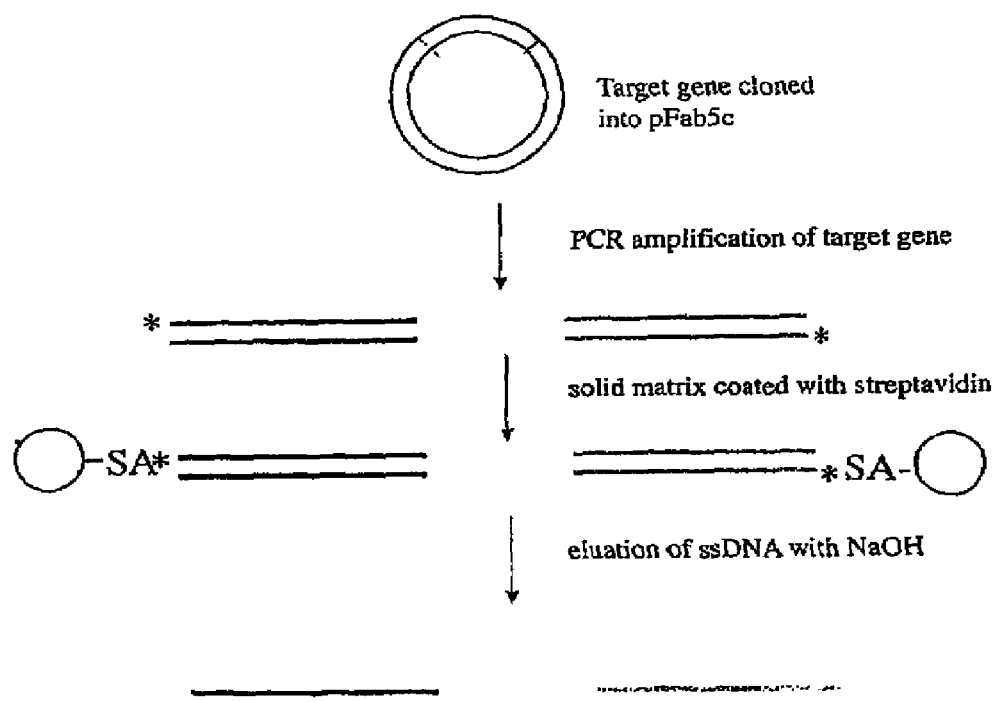
FIG. 2 shows the principle steps in preparation of single-stranded DNA using biotin.
Figure 3:
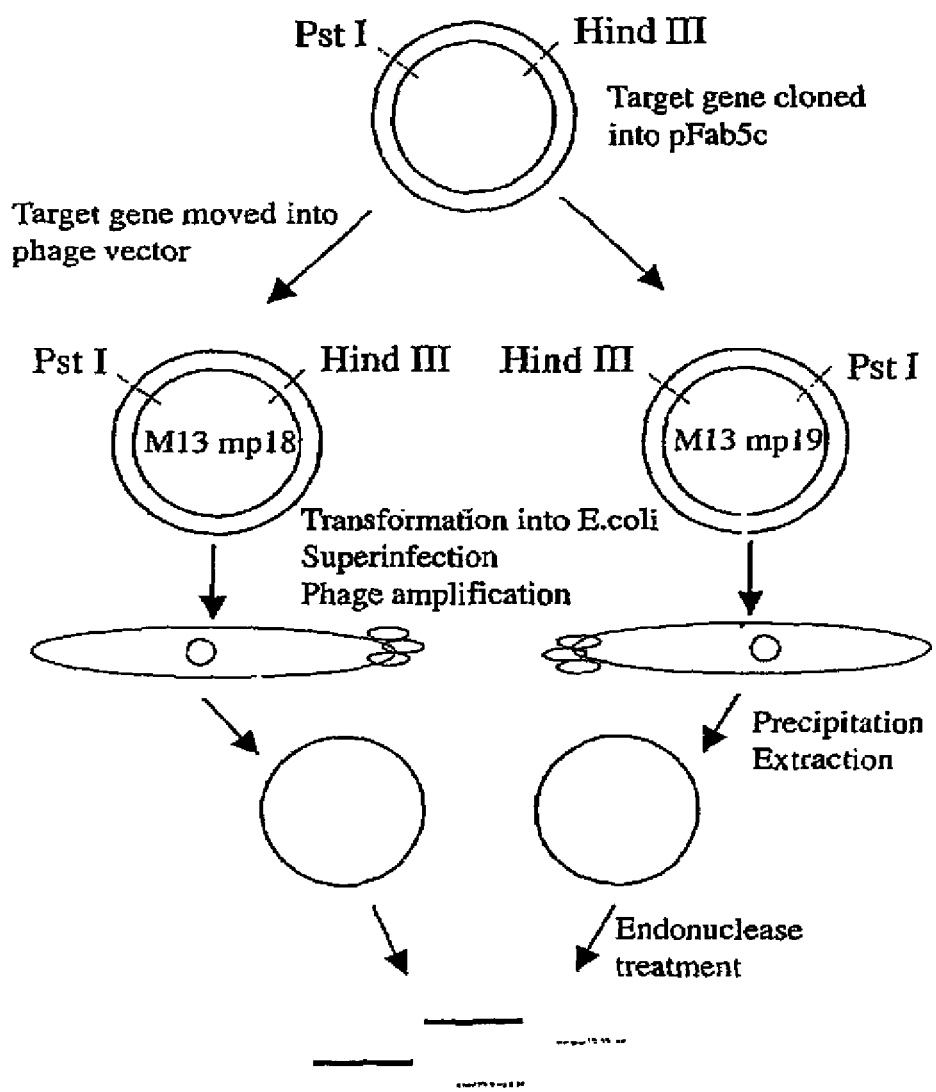
FIG. 3 shows the principle steps in the preparation of single-stranded DNA using phage.
Figure 4:
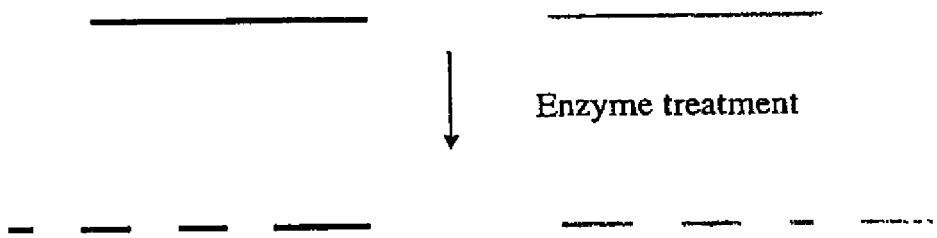
FIG. 4 shows the principle steps generating single-stranded DNA fragments using exonuclease treatment.
Figure 5:
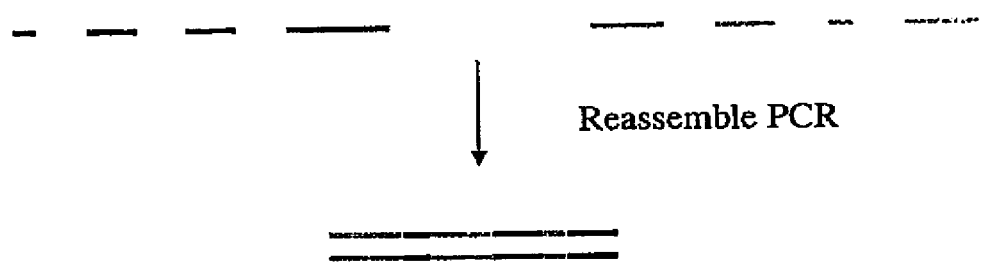
FIG. 5 shows the principle steps for assembly of single-stranded DNA fragments using PCR.

The DNA shuffling procedure can be illustrated by the steps shown in FIGS. 1 to 5. The gene encoding the protein of interest (X) in the plasmid pFab5chis is used in this example. Random mutations are introduced by error prone PCR. Single-stranded DNA is prepared. This can be carried out by either biotinylated primers or by the use of phage being able to pack single-stranded DNA, as discussed above. The coding and the non-coding ssDNA strands are prepared in different reactions (A and B). The ssDNA strands from either reactions are subjected to separate enzymatic treatment using e.g. BAL 31. By mixing the two pools of single-stranded DNA fragments in equimolar amounts the gene can be reassembled in a shuffled nature and in many versions by the use of two subsequent PCR reactions, where the first reaction contains no primers. After cloning this library of reassembled genes in pY, selections can be performed to achieve the improved molecule of interest.

A more detailed description of examples of the present invention is given below.

Example 1

Reagents

AmpliTaq® polymerase was purchased from Perkin-Elmer Corp., dNTPs from Boehringer Mannheim Biochemica (Mannheim, Germany), and BAL31 Nuclease from New England Biolabs Inc. (Beverly, USA). All restriction enzymes were purchased from New England Biolabs Inc. (Beverly, USA). Ethidium bromide was purchased from Bio-Rad Laboratories (Bio-Rad Laboratories, Hercules, Calif., USA). T4 DNA Ligase was purchased from New England Biolabs Inc. (Beverly, USA). EDTA and EGTA was purchased from Kebo Lab (Sweden).

All primers were designed in the laboratory and obtained from Life Technologies (Täby, Sweden) and SGS-DNA (Köping, Sweden).

PCR

All Polymerase Chain Reactions (PCR) were carried out in a automatic thermocycler (Perkin-Elmer Cetus 480, Norwalk, Conn., USA). PCR techniques for the amplification of nucleic acid are described in U.S. Pat. No. 4,683,195. References for the general use of PCR techniques include Mullis et al., Cold Spring Harbor Symp. Quant. Biol., 51:263, (1987), Ehrlich (ed), PCR technology, Stockton Press, NY, 1989, Ehrlich et al., Science, 252:1643-1650, (1991), "PCR protocols; A Guide to Methods and Applications", Eds. Innis et al., Academic Press, New York, (1990).

Sequencing

All constructs have been sequenced by the use of BigDye Terminator Cycle Sequencing kit (Perkin-Elmer, Elmervill, Calif., USA). The sequencing was performed on a ABI Prism 377 DNA Sequencer.

Agarose Electrophoresis

Agarose electrophoresis of DNA was performed with 2% agarose gels (AGAROSE (FMC Bioproducts, Rockland, Me., USA)) with 0.25 µg/ml ethidium bromide in Tris-acetate buffer (TAE-buffer 0.04M Tris-acetate, 0.001M EDTA). Samples for electrophoresis were mixed with a sterile filtrated loading buffer composed of 25% Ficoll and Bromphenolic blue and loaded into wells in a the 2% agarose gel. The electrophoresis was run at 90 V for 45 minutes unless otherwise stated in Tris-acetate buffer with 0.25 µg/ml ethidium bromide. Bands of appropriate size were gel-purified using the Qiaquick Gel Extraction Kit (Qiagen GmbH, Hilden, Germany) when needed. As molecular weight standard, DNA molecular weight marker 1 kb ladder (Gibco BRL) was used. The DNA-concentration of the gel extracted products were estimated using a spectrophotometer.

Bacterial Strains

The *Escherichia coli*-strain TOP10F' was used as a bacterial host for transformations. Chemically competent cells of this strain were produced basically as described Hanahan, D. 1983. Studies on transformation of *Escherichia coli* with plasmids. J. Mol. Biol. 166: 557-580. Electrocompetent cells of this bacterial strain were produced (Dower, W. J., J. F. Miller, and C. W. Ragsdale. 1988: High efficiency transformation of *E. coli* by high voltage electroporation. Nucleic Acids Res. 16:6127).

Plasmids

All genetic manipulations were performed in pFab5chis according to Molecular cloning; a laboratory manual (Second Edition, Cold Spring Harbor Laboratory Press, 1989). This vector is designed to harbour any scFv gene inserted between SfiI and NotI sites. The SfiI site is located in the pelB leader and the NotI site is located just after the VL region, such that VH-linker-VL is inserted. In this case, an antibody directed to CD40 was used.

Primers

Two biotinylated primers surrounding the antibody gene of pFabSchis were designed with the following sequences including designated unique restriction sites:

```
1736 SfiI forward primer:                SEQ ID NO:1
5'-ATT ACT CGC GGC CCA GCC GGC CAT GGC CCA CAG GTC
AAG CTC GA and 1735 NotI reversed primer:               SEQ ID NO:2
5'-TTA GAG CCT GCG GCC GCC TTG TCA TCG TCG TCC TT
```

Two non-biotinylated primers surrounding the antibody gene of pFabSchis were designed with the following sequences including designated unique restriction sites:

```
1664 SfiI forward primer:                SEQ ID NO:3
5'-ATT ACT CGC GGC CCA GCC GGC CAT GGC CCA CAG GTC
AAG CTC GA and 1635 NotI reversed primer:               SEQ ID NO:4
5'-TTA GAG CCT GCG GCC GCC TTG TCA TCG TCG TCC TT
```

Standard PCR

Standard PCR reactions were run at 25 cycles consisting of following profile: denaturation (94° C., 1 minute), primer annealing (55° C., 1 minute) and extension (72° C., 3 minutes). Each PCR reaction contained 10 mM Tris-HCl, pH 8.3, 50 mM KCl, 1.5 mM MgCl$_2$, 200 µM dNTP, 1 µM forward primer, 1 µM reverse primer, 1.25 U AmpliTaq® thermostable DNA polymerase (Perkin-Elmer Corp.), and 50 ng template in a final volume of 100 µl.

Error Prone PCR

The error prone PCR reactions were carried out in a 10× buffer containing 500 mM NaCl, 100 mM Tris-HCl, pH 8.8, 5 mM MgCl$_2$ 100 µg gelatine (according to Kuipers et al., Nucleic Acids Res. 1991, Aug. 25;19 (16):4558 but with MgCl$_2$ concentration increased from 2 mM to 5 mM).

For each 100 µl reaction the following was mixed:

| | |
|---|---|
| dATP 5 mM | 5 µl |
| dGTP 5 mM | 5 µl |
| dTTP 10 mM | 10 µl |
| dCTP 10 mM | 10 µl |
| 20 µM 3' primer | 1.5 µl |
| 20 µM 5'-primer | 1.5 µl |
| 10 × Kuipers buffer | 10 µl |
| sterile mp H$_2$O | 46.3 µl |

The template in pFab5chis vector was added at an amount of 50 ng. 10 µl of 10 mM MnCl$_2$ was added and the tube was checked that no precipitation of MnO$_2$ occurred. At last 5 Units of Taq enzyme was added. The error prone PCR was run at the following temperatures for 25 cycles without a hot start: 94° C. 1', 45° C. 1', 72° C. 1', +72° C. for 7 minutes. The resulting product was an error proned insert over the protein of approximately 750 bp. This insert was purified with Gibco PCR purification kit, before further treatment.

Generation of Single-Stranded DNA by Biotinylated Primers

The fragment of interest was amplified by two separate PCR reactions.

These reactions can be standard PCR as described above or error prone PCR also as described above. The primers should be designed so that in one reaction the forward primer is biotinylated and in the other reaction the reverse primer is biotinylated. For example, PCR reactions with A) primers 1736 and 1635 and B) primers 1664 and 1735, with the above mentioned profile was performed for 25 cycles with pFab5chis-antibody as template. This yielded PCR-products of approximately 750 bp where in A the upper strand was biotinylated and in B the lower strand was biotinylated.

The non-biotinylated strands were retrieved by purification using a solid matrix coated with streptavidin e.g. Dynabeads. The magnetic beads are washed and equilibrated with PBS/1% BSA and B&W buffer containing 5 mM Tris pH 7.5, 1 M NaCl, and 0.5 mM EGTA. 100 µl of each PCR product is mixed with 100 µl beads dissolved in 2× B&W buffer and incubated at room temperature for 15 minutes with rotation. Unbound PCR products are removed by careful washing twice with B&W. The non-biotinylated strand of the captured DNA is eluted by alkaline denaturation by letting the DNA incubate with 25 µl 0.1 M NaOH for 10 minutes in room temperature. The solution is separated from the beads and neutralised with 7.5 µl 0.33 M HCl and 2.5 µl 1 M Tris pH 8.

Generation of Single-stranded DNA Using Phage

The fragment of interest was cloned into bacteriophage M13 vectors M13 mp18 and M13 mp19 using PstI/HindIII restriction enzymes. The bacteriophage were propagated using *Escherichia* constrain TOP10F' according to conventional methods. Single-stranded DNA for the upper strand was prepared from bacteriophage vector M13 mp18 and single-stranded DNA for the lower strand was prepared from bacteriophage vector M13 mp19. Briefly, 1.5 ml of an infected bacterial culture was centrifuged at 12 000 g for 5 minutes at 4° C. The supernatant was precipitated with 200 µl 20% PEG8000/2.5 M NaCl. The pelleted bacteriophage was resuspended in 100 µl TE. 50 µl phenol equilibrated with Tris-Cl (pH 8.0) was added and the sample was vortexed. After centrifugation at 12 000 g for 1 minute at RT the upper phase, containing the DNA, was transferred and precipitated with ethanol. The DNA pellet was dissolved in 50 µl TE (pH 8.0) and stored at −20° C. (Sambrook et al. Molecular Cloning, A laboratory manual $2^{nd}$ edition. Cold Spring Habor Laboratory Press. 1989, chapter 4). Single-stranded DNA prepared from phage is circular and must be opened prior to BAL31 treatment. This can be performed with an endonuclease able to cleave single-stranded DNA.

Generation of Single-stranded DNA Using Asymmetric PCR

PCR products are purified using a spin column to remove excess primers from the previous PCR. 150 ng of the purified product is used as template in a linear amplification carried out in 100 µl of 1xGeneAmp® 10× PCR buffer containing 1.5 mM MgCl2 (Applied Biosystems), 200 µM of each dNTP (New England BioLabs), 1.25 U AmpliTaq® DNA Polymerase (Applied Biosystems) and 1.0 µM of a single primer. PCR cycle conditions are: denaturation at 94° C. for 1 minute, 35 cycles of 94° C. for 30 seconds, 55° C. for 30 seconds, 72° C. for 1 minute followed by extension at 72° C. for 7 minutes.

Asymmetric PCR products are size separated from double stranded template on a 1% agarose gel and purified using Qiaquick Gel Extraction Kit (Qiagen).

Generation of Single-stranded Fragmented DNA Using BAL 31

The ssDNA strands (containing upper and lower strands, respectively) were subjected to separate enzymatic treatment using e.g. BAL 31. Each digestion reaction contained 0.02 µg/µl ssDNA, 600 mM NaCl, 20 mM Tris-HCl, 12 mM $CaCl_2$, 12 mM $MgCl_2$, 1 mM EDTA pH 8.0 and BAL 31 at various enzyme concentrations ranging from 0.1-5 U/ml. The reactions were incubated at 30° C. and fractions of digested ssDNA were collected sequentially at 10, 30, 60 and 120 seconds or longer. The reactions were stopped by addition of EDTA and heat treatment at 65° C. for 10 minutes. The ssDNA fragments were purified by phenol/chloroform extraction and ethanol precipitated. The ssDNA are resuspended in 10 mM Tris pH 8.0.

The digestion pattern was evaluated by 1% agarose gel electrophoresis.

Purification of Digestion Produced Fragments:

Digested DNA fragments were purified by phenol/chloroform/isoamylalcohol extraction. 50 µl of buffered phenol was added to each tube of 100 µl sample together with 50 µl of a mixture of chloroform and isoamylalcohol (24:1). The tubes were vortexed for 30 seconds and then centrifuged for 1 minute in a microfuge at 14000 r.p.m. The upper phase was then collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 µl of sterile water.

Analysis of Digestion Produced Purified Fragments on Agarose Gel

5 µl of the dissolved pellet from each time point and from the blank were mixed with 2.5 µl of loading buffer (25% Ficoll and Bromphenolic blue) and loaded into wells in a 2% agarose gel. The electrophoresis of the different time points were performed as above.

Reassembly of Full Length Fragments

Reassembly of the ssDNA fragments is achieved by two sequential PCR reactions. The first PCR reaction should contain 10 mM Tris-HCl, pH 8.3, 50 mM KCl, 1.5 mM $MgCl_2$, 200 µM dNTP, 0.3 U Taq polymerase and 2 µl BAL31 treated sample, all in a final volume of 25 µl, and subjected to 5 cycles with the following profile: 94° C. for 1 minute, 50° C. for 1 minute and 72° C. for 2 minutes+72° C. for 5 minutes. The second PCR reaction should contain 10 mM Tris-HCl, pH 8.3, 50 mM KCl, 1.5 mM $MgCl_2$, 200 µM dNTP, 0.6 U Taq polymerase, 1 µM forward primer, 1 µM reverse primer, and 5 µl sample from the first PCR reaction, all in a final volume of 50 µl, and subjected to 15 cycles with the following profile: 94° C. for 1 minute, 55° C. for 1 minute and 72° C. for 2 minutes+72° C. for 7 minutes. The resulting products can be evaluated by agarose gel electrophoresis.

Restriction Digestion of Reassembled Fragment and Plasmid with SfiI and NotI

The reassembled fragment and the plasmid pFab5chis were first cleaved with SfiI by using NEB buffer 2 including BSA and 11 U enzyme/µg DNA. The reaction was carried out for 4 h at 50° C. After this the DNA was cleaved with NotI by adding conversion buffer and 6 U enzyme/µg DNA. This reaction was carried out for 37° C. overnight.

Gel Purification of Restriction Digested Vector and Restriction Digested Reassembled Fragment The cleavage reactions were analysed on a 1% agarose gel. The restriction digested insert showed a cleavage product of about 750 bp. This corresponds well with the expected size. The band of the cleaved insert and plasmid was cut out and gel-extracted as previously described.

Ligation of Reassembled Restriction Digested Fragment with Restriction Digested pFab5chis Purified cleaved pFab5chis was ligated with purified reassembled restriction digested fragment at 12° C. water bath for 16 hours. 50 µl of the vector was mixed with 50 µl of the insert and 15 µl of 10× buffer (supplied with the enzyme), 7.5 µl ligase (5 U/µl) and sterile water to a final volume of 150 µl. A ligation of restriction digested pFab5chis without any insert was also performed in the same manner.

Transformation of Chemically Competent E coli TOP10F' with the Ligated Reassembled Insert and pFab5chis The ligation reactions were purified by phenol/chloroform extraction as described above. The upper phase from the extraction was collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r.p.m. The pellet was washed once with 70% ethanol and then re-dissolved in 10 µl of sterile water. 5 µl of each ligation was separately mixed with 95 µl chemically competent E coli TOP10F' incubated on ice for 1 hour and then transformed (Sambrook et al. Molecular Cloning, A laboratory manual $2^{nd}$ edition. Cold Spring Habor Laboratory Press, 1989). After one hour's growth the bacteria from the two transformations were spread onto ampicillin containing agar plates (100 µg/ml). The plates were grown upside-down in a 37° C. incubator for 14 hours.

Example 2

Recombination Frequencies; Comparison of dsDNA and ssDNA

In further comparable experiments, three scFv antibody fragments were used in a recombination experiments, either as dsDNA or as ssDNA.

dsDNA

The three scFv genes were each amplified in PCR using forward and reverse primers and standard PCR procedure. The size of the bands was confirmed with agarose electrophoresis and the rest of the amplified PCR products were purified using Concert PCR purification kit (Gibco). The dsDNA from the three scFv were mixed in equimolar amounts and treated with BAL31. Each digestion reaction contained dsDNA at a concentration of 0.02 µg/µl reaction volume, 600 mM NaCl, 20 mM Tris-HCl, 12 mM $CaCl_2$, 12 mM $MgCl_2$, 1 mM EDTA pH 8.0 and BAL31 at various enzyme concentrations (using 4, 20 or 100 U enzyme/ml reaction volume). The reactions were incubated at 30° C. and fractions of digested dsDNA were collected sequentially at 10, 30, and 50 minutes. The reactions were stopped with EDTA and heat treatment (alternatively, an EDTA-free heat inactivation protocol may be used; see below) and purified using phenol/chloroform extraction and ethanol precipitation. The dsDNA samples were resuspended in 10 mM Tris pH 8.0.

Keeping each time point separate, the samples were subjected to reassembly PCR (for this reassembly 60 ng DNA is used) and amplification PCR according to the protocol, and cloned in pGEM (Product No A362A, Promega, Madison, USA). Eighteen clones from each time point were sequenced and the number and frequency of recombinations were determined.

Heat Inactivation of Exonuclease Digestions

A protocol to stop the BAL31 reaction without using EDTA has been established. This heat inactivation protocol avoids using phenol/chloroform extraction, which is hazardous to health and also causes loss of material.

In brief, the sample is incubated for 10 minutes at 95 C. and then put directly in ice, to stop the enzymatic reaction. After this the sample can be directly precipitated using ethanol.

ssDNA

The three scFv genes were each amplified in two PCR reactions using primer pairs forward/reverse-biotin and forward-biotin/reverse using standard PCR procedure. The size of the bands were confirmed with agarose electrophoresis and the rest of the amplified PCR products were purified using Concert PCR purification kit (Gibco). Single-stranded DNA was obtained using magnetic beads according to the protocol, achieving three sense strands and three antisense strands. The sense strands and the antisense strands, respectively, from the three scFv were mixed in equimolar amounts and treated with BAL31 according to the protocol (using 1.25 or 11 U enzyme/ml reaction volume and ssDNA at a concentration of 0.015 µg/µl reaction volume) and samples were taken out at 0 (i.e. undigested), 10, 30 and 50 minutes. The reactions were stopped with EDTA and heat treatment and purified using phenol/chloroform extraction and ethanol precipitation. Keeping each time point separate, but mixing sense and antisense strands, the samples were subjected to reassembly PCR (for this reassembly 60 ng DNA is used) and amplification PCR according to the protocol, and cloned in pGEM. Eighteen clones from each time point were sequenced and the number and frequency of recombinations were determined.

Results

Figure 6:
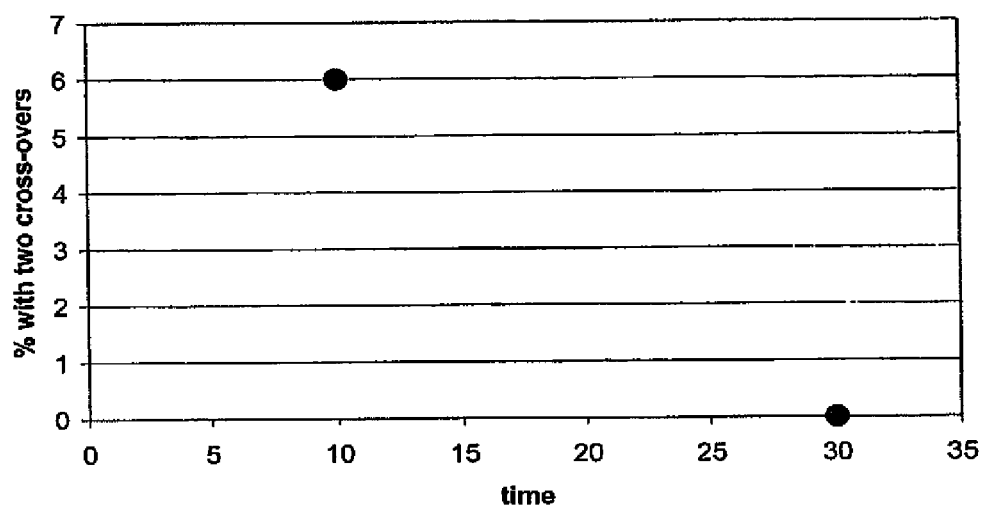
FIG. 6 shows the % of recombinants formed having one cross-over following digestion of dsDNA with 20 U/ml BAL31 for varying periods of time.
Figure 7:
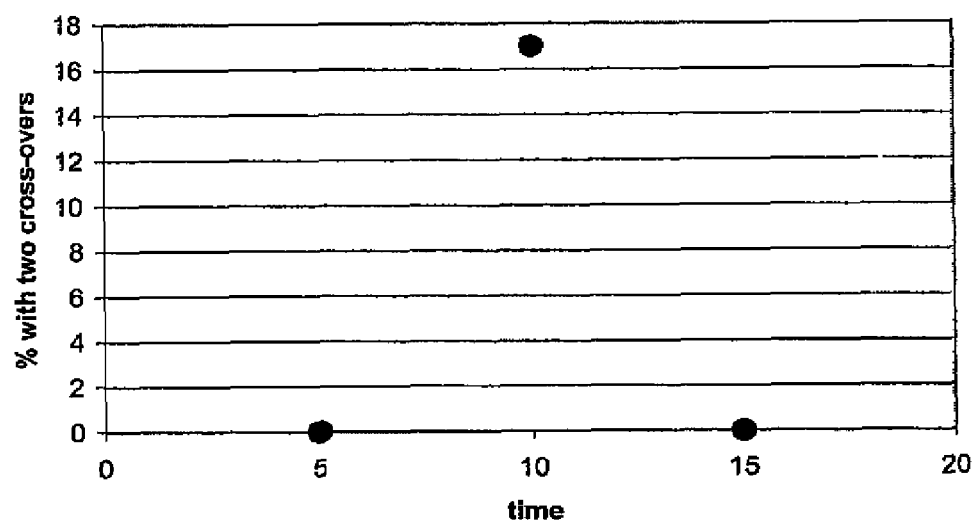
FIG. 7 shows the % of recombinants formed having two cross-overs following digestion of dsDNA with 20 U/ml BAL31 for varying periods of time.

The highest frequency of recombination using dsDNA was achieved using 20 U enzyme/ml reaction volume (containing 0.02 µg/µl DNA) and treating for 10 minutes. This gave 39% of the clones with one cross-over (FIG. 6) and 17% of the clones with two cross-overs (FIG. 7). Using 4 U enzyme/ml gave no cross-overs independent of time for fragmentation and 100 U enzyme/ml resulted in complete fragmentation into very small fragments, as indicated by the failure to regain the full-length gene during reassembly.

Figure 8:
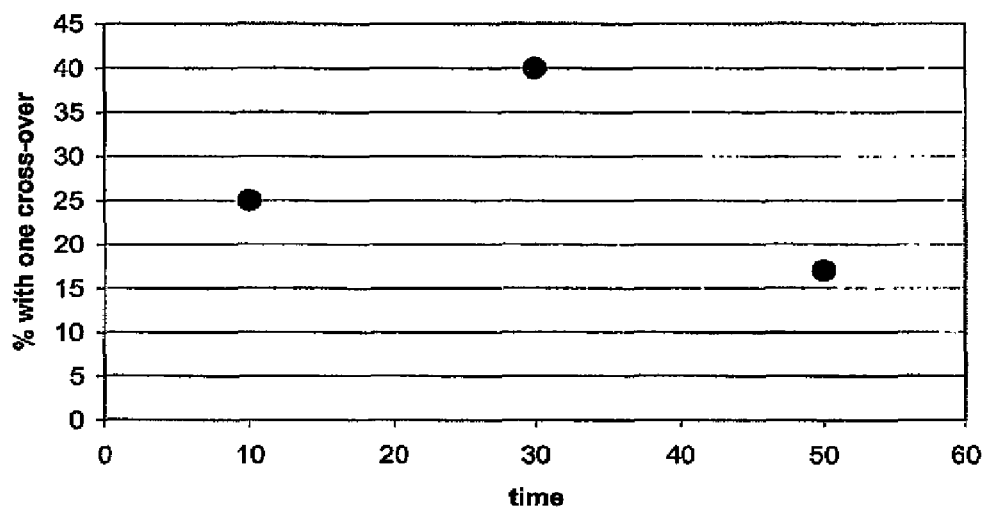
FIG. 8 shows the % of recombinants formed having one cross-over following digestion of ssDNA with 1.25 U/ml BAL31 for varying periods of time.
Figure 9:
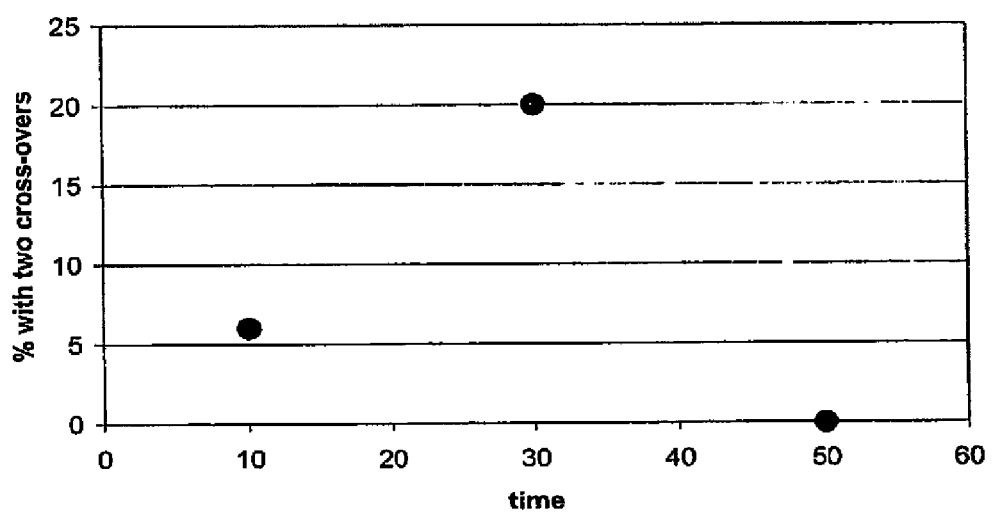
FIG. 9 shows the % of recombinants formed having two cross-overs following digestion of ssDNA with 1.25 U/ml BAL31 for varying periods of time.
Figure 10:
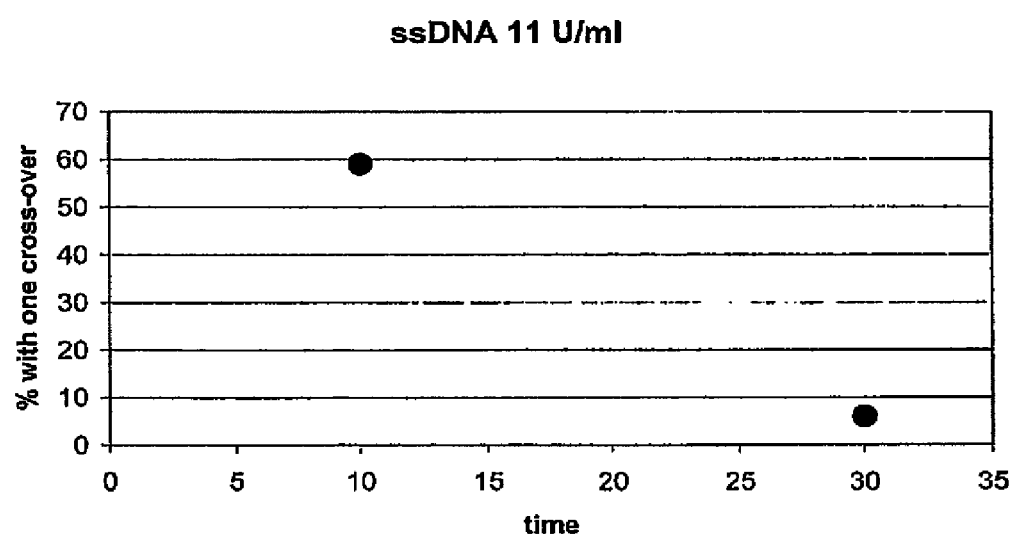
FIG. 10 shows the % of recombinants formed having one cross-over following digestion of ssDNA with 11 U/ml BAL31 for varying periods of time.
Figure 11:
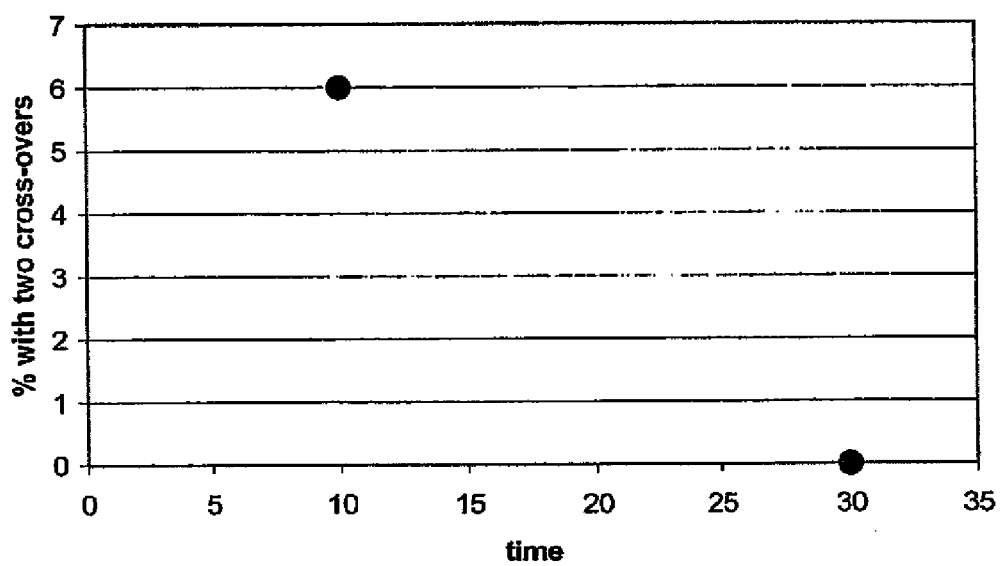
FIG. 11 shows the % of recombinants formed having two cross-overs following digestion of ssDNA with 11 U/ml BAL31 for varying periods of time.

The results from the experiments using ssDNA are shown in FIGS. 8 to 10. FIG. 8 shows 1.25 U/ml BAL31 and clones with one cross-over, FIG. 9 shows 1.25 U/ml BAL31 and clones with two cross-overs. FIG. 10 shows 11 U/ml BAL31 and clones with one cross-over, and FIG. 11 shows 11 U/ml BAL31 and clones with two cross-overs.

The highest frequency of recombination giving one cross-over using ssDNA was achieved using 11 U enzyme/ml and treating for 10 minutes (FIG. 10). 59% of the clones had one cross over. The highest frequency of recombination giving two cross-overs using ssDNA was achieved using 1.25 U enzyme/ml and treating for 30 minutes (FIG. 9). 20% of the clones had two cross overs.

Conclusions and Comments

These data clearly show that a higher frequency of recombination is achieved using ssDNA. The three scFv used have the same framework sequences, indicating that the number of cross overs reported may be higher due to cross overs in regions where no sequence difference will result. These experiments using ssDNA were carried out in a non-optimal fashion for showing maximum recombination, since all strands from all three molecules were mixed. Mixing the sense strand from one scFv with the antisense strand from another scFv would produce higher frequencies of cross overs, see Example 3 below. Also, each time point was here kept separate and it would be logical to estimate the frequency of cross overs to increase if different time points, i.e. different fragments sizes, are mixed.

Example 3

Recombination Frequencies; Homology Dependence Using ssDNA

To investigate the homology required to achieve cross-over we set up experiments to recombine four scFv (designated SMUC159, CT17, AE11 and MO152) making up three pairs with different homologies, as follows:

| | |
|---|---|
| SMUC159 - CT17 | 92% |
| SMUC159 - AE11 | 70% |
| SMUC159 - MO152 | 60% |

The four scFv genes were each amplified in two PCR reactions using primer pairs forward/reverse-biotin and forward-biotin/reverse using standard PCR procedure. The size of the bands were confirmed with agarose electrophoresis and the rest of the amplified PCR products were purified using Concert PCR purification kit (Gibco). Single-stranded DNA was obtained using magnetic beads according to the protocol, achieving four sense strands and four antisense strands. Each strand was treated with BAL31 according to the protocol (using 4.2 or 12.5 U enzyme/ml) and samples were taken out at 0, 10, 30 and 50 minutes, or 0, 15, 30, 45 and 60 minutes. The reactions were stopped with EDTA and heat treatment and purified using phenol/chloroform extraction and ethanol precipitation. Keeping each time point separate, but mixing sense and antisense strands forming the pairs as indicates above, the samples were subjected to reassembly PCR and amplification PCR according to the protocol, and cloned in pGEM. Fifteen clones from each time point were sequenced and the number and frequency of recombination were determined.

Results

Cross overs were identified in all combinations of scFv, indicating that as low as 60% homology is enough to achieve recombination.

Example 4

Improved Control of Fragment Size Using Exonucleases (A) Exonucleases

We use exonucleases, e.g. BAL31, exonuclease I, exonuclease V, exonuclease VII, exonuclease T7 gene 6, bacteriophage lambda exonuclease, and exonuclease Rec $J_f$ for fragmentation in the methods of the present invention. These enzymes cleave off one nucleotide at a time, either from the 5' end or from the 3'end or from both ends. The reaction can be stopped using EDTA or heat inactivation (see above), depending on the enzyme used. This means that fragments of all possible sizes, differing with only one nucleotide, can be obtained.

The following examples demonstrate how exonuclease digestion allows the creation of fragments of various and controllable sizes depending on the conditions used.

BAL31

Single-stranded DNA was digested with BAL31 according to the protocol in Example 1, with an enzyme concentration of 4.2 U/ml reaction volume and ssDNA concentration of 0.008 µg/µl reaction volume.

In a typical experiment, about 300 ng DNA is isolated at each time point of BAL31 treatment. An agarose electrophoresis gel image of such an experiment with untreated ssDNA in lane 4 and ssDNA treated for 10 minutes in lane 3, for 30 minutes in lane 2 and for 50 minutes in lane 1 was prepared. Lane 5 is the molecular weight (MW) standard.

Figure 12:
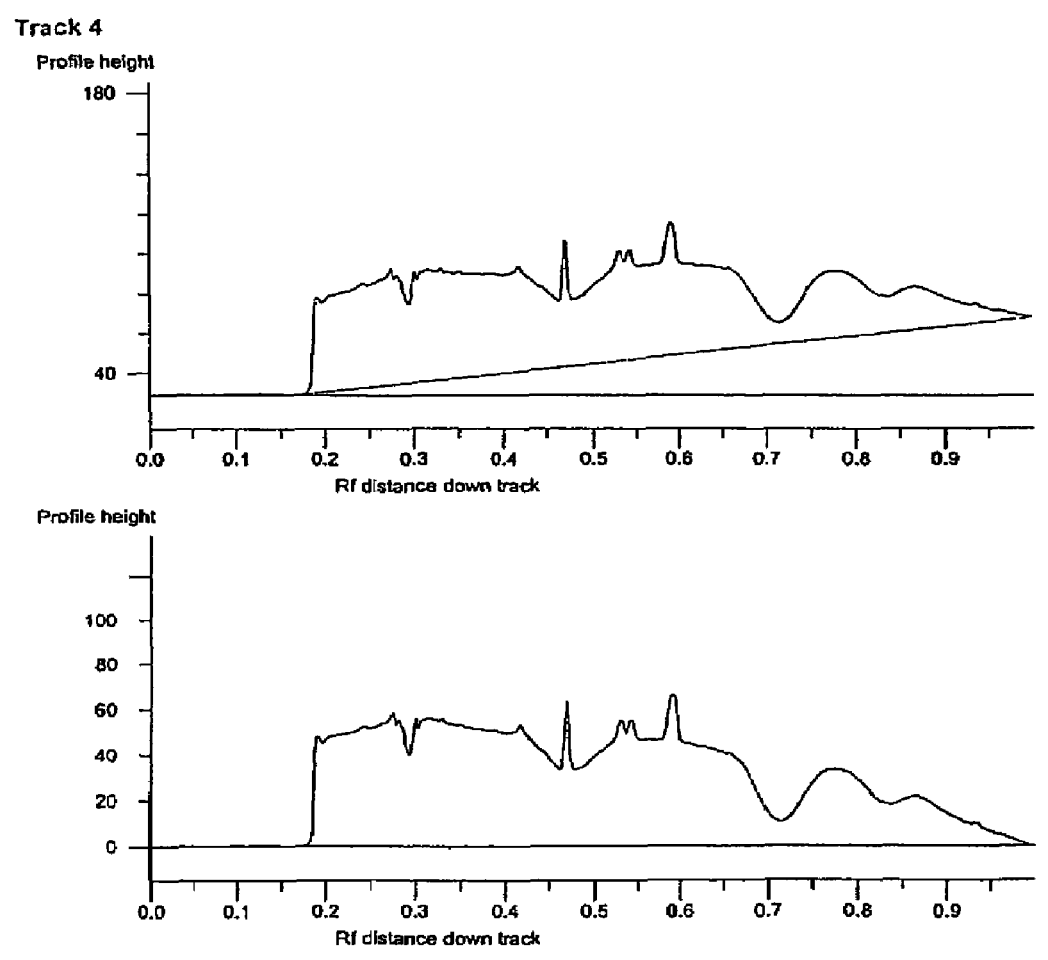
Figure 14:
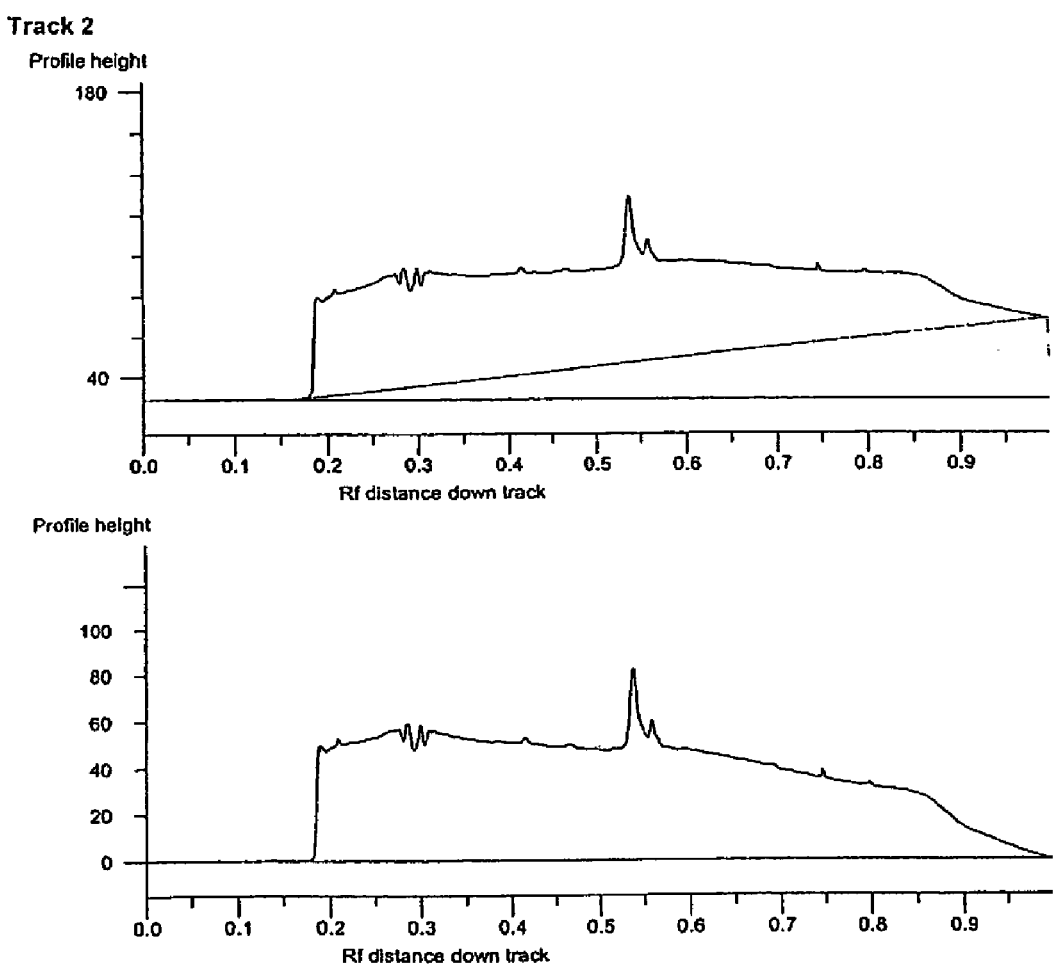
FIG. 14 shows the gel chromatograms for lane 2.

FIGS. 12 to 14 show the gel chromatograms of the lanes, respectively. FIG. 12 is the untreated material and the multiple peaks refer to different conformations of the ssDNA. FIG. 13 corresponds to lane 3 and material treated for 10 minutes. The material was heat treated to stop the enzymatic reaction, and thus resolving the different conformations, and one peak of a distinct size is shown. FIG. 14 corresponds to lane 2 and material treated for 30 minutes.

Here it is clear that the peak corresponding to larger fragments is decreasing and a peak of smaller DNA fragments has appeared.

Exonuclease VII

Single-stranded DNA was digested with exonuclease VII using an enzyme concentration of 7.7 U/ml reaction volume and ssDNA concentration of 0.008 µg/µl reaction volume. The reaction buffer comprised 67 mM potassium phosphate (pH 7.9), 10 mM mercaptoethanol, 6.7 mM $MgCl_2$ and 8.3 mM EDTA.

The reaction was allowed to proceed at 37° C. for 10, 20 and 30 minutes, before being stopped by heat inactivation (95° C. for 5 minutes).

The fragmentation pattern using exonuclease VII was determined. Lane 1 is MW standard, lane 2 is untreated ssDNA, lane 3 is ssDNA fragmented with exonuclease VII for 10 minutes, lane 4 is ssDNA fragmented with exonuclease VII for 20 minutes, and lane 5 is ssDNA fragmented with exonuclease VII for 30 minutes. This shows that the fragment sizes are decreased by time.

Exonuclease Rec $J_f$

Single-stranded DNA was digested with exonuclease Rec $J_f$ using an enzyme concentration of either 2.5 U/ml reaction volume or 10 U/ml reaction volume and ssDNA at a concentration of 0.007 µg/µl reaction volume, corresponding to 0.36 U enzyme/µg DNA and 1.4 U enzyme/µg DNA, respectively. The reaction buffer comprised 50 mM NaCl, 10 mM Tris.HCl, 10 mM $MgCl_2$ and 1 mM dithiothreitol, at pH 7.9

The reaction was allowed to proceed at 37° C. for 10, 20 and 30 minutes, before being stopped by heat inactivation (95° C. for 5 minutes).

The fragmentation pattern using exonuclease Rec $J_f$ at 036 U/microgram ssDNA was shown. Lane 1 untreated ssDNA, lane 2 is ssDNA fragmented with exonuclease Rec $J_f$ for 10 minutes, lane 3 is ssDNA fragmented with exonuclease Rec $J_f$ for 20 minutes, and lane 4 is ssDNA fragmented with exonuclease Rec $J_f$ for 30 minutes. This shows that the fragment sizes are decreased by time. The enzyme concentration is increased 4 times (1.4 U/microgram ssDNA) and the fragmentation pattern was determined from 0 to 30 minutes, showing a higher degree of fragmentation. This shows that both time and enzyme concentration can be used to control the fragmentation.

(B) Endonucleases

Conventional DNA shuffling methods typically use DNase I for fragmentation (for example, see Stemmer, 1994, Nature 370:389-391). DNase I cleaves DNA in an endonucleolytic fashion at sites adjacent to pyrimidines. Consequently, not all possible fragment sizes can be obtained.

Moreover, using magnesium in the reaction buffer, a homologous mix of mono- and oligomers is obtained. Hence, different methods such as gel agarose electrophoresis purification or gel filtration need to be used in order to isolate fragments of different sizes. Often fragments of small size or a mix of small and larger fragments are desired to optimise recombination. However, these purification methods introduce single-stranded nicks in the double-stranded PCR products. Fragments of a particular size purified on a gel would thus consist of dsDNA with a large number of single-stranded nicks, which would give rise to many smaller fragments upon denaturation. This means that many of the single-stranded fragments generated upon denaturation would be too short to function as primers during the annealing, resulting in a great loss of product.

Using manganese in the reaction buffer creates fragments of sizes smaller than 50 bp and no gel purification is needed. However, here you are restricted to use only small fragments and these can not be mixed with larger fragments, something that would probably increase the recombination frequency.

The problems associated with the use of endonucleases are demonstrated in the following experiments:

DNase I

DNA was digested for 5 minutes with DNase I at a concentration of 0.15 U/µg DNA.

Magnesium and manganese buffers were compared when fragmenting with DNase I. Lane 1 is MW standard, lane 2 is untreated ssDNA in Mg buffer, lane 3 is ssDNA fragmented with DNase I in Mg buffer according to Stemmer (1994) Nature 370:389-391, lane 4 is untreated ssDNA in Mn buffer and lane 5 is ssDNA fragmented with DNase I in Mn buffer according to Kikuchi et al. (2000) Gene 243:133-137. When using Mg buffer and conditions according to the Stemmer and Kikuchi papers, no fragmentation occurs. Moreover, when using Mn buffer and conditions according to the Stemmer and Kikuchi papers, all material is totally fragmented within only a few minutes.

In an attempt to obtain fragments of different sizes we decided to use Mg buffer and increase the enzyme concentration using DNase I. Lane 1 is the MW standard. Lane 6 is untreated ssDNA. Lane 12 is ssDNA treated according to the Stemmer and Kikuchi papers, using 0.15 U enzyme/microgram DNA and lane 13 is the same material treated with 1 U enzyme/microgram DNA (i.e. six times more enzyme).

Figure 15:
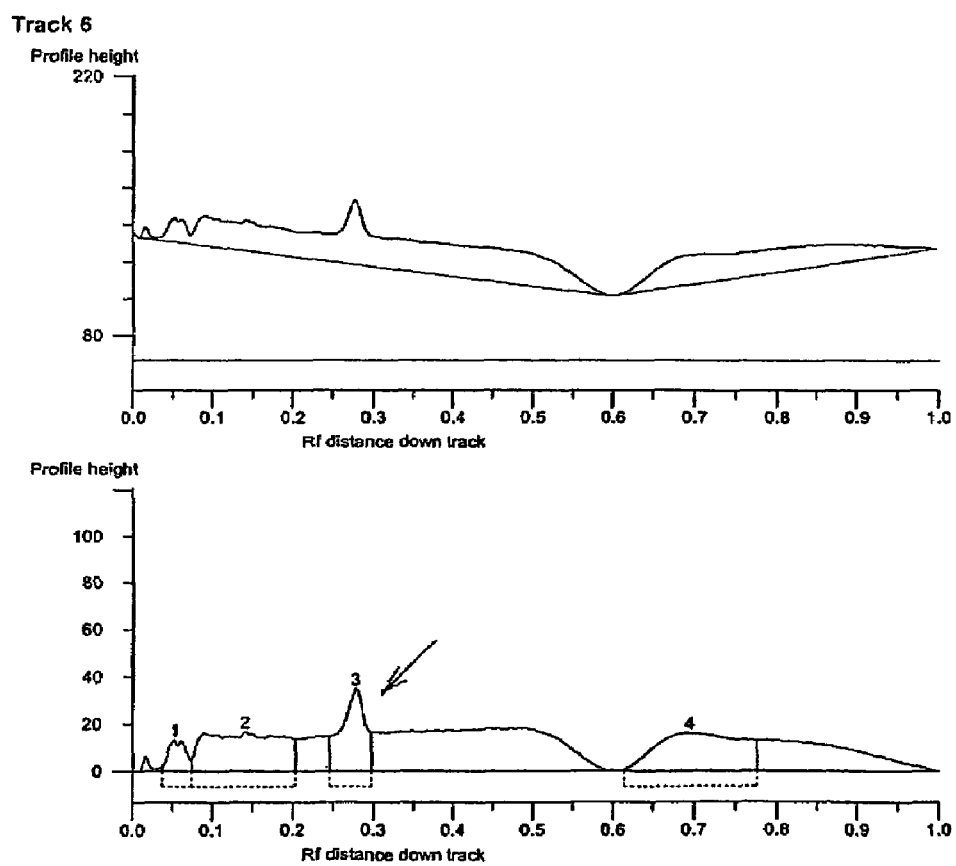
FIG. 15 shows the gel chromatograms for lane 6.
Figure 16:
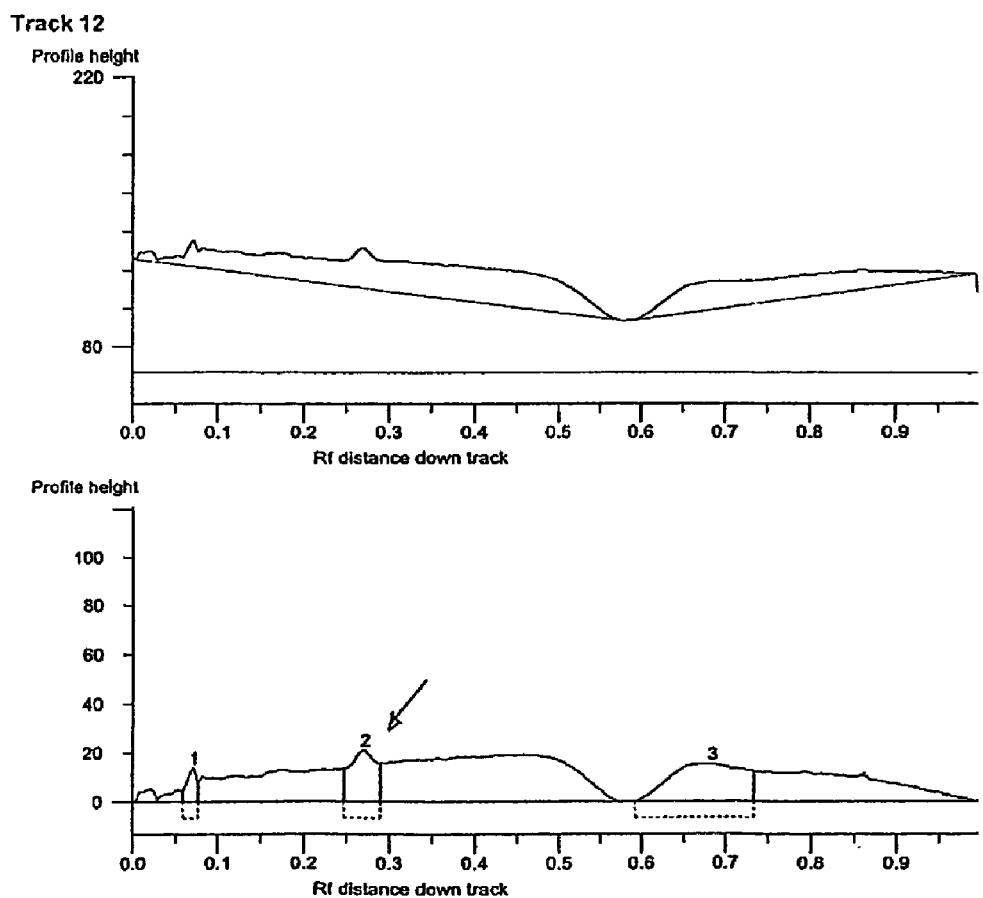
FIG. 16 shows the gel chromatograms for lane 12.
Figure 17:
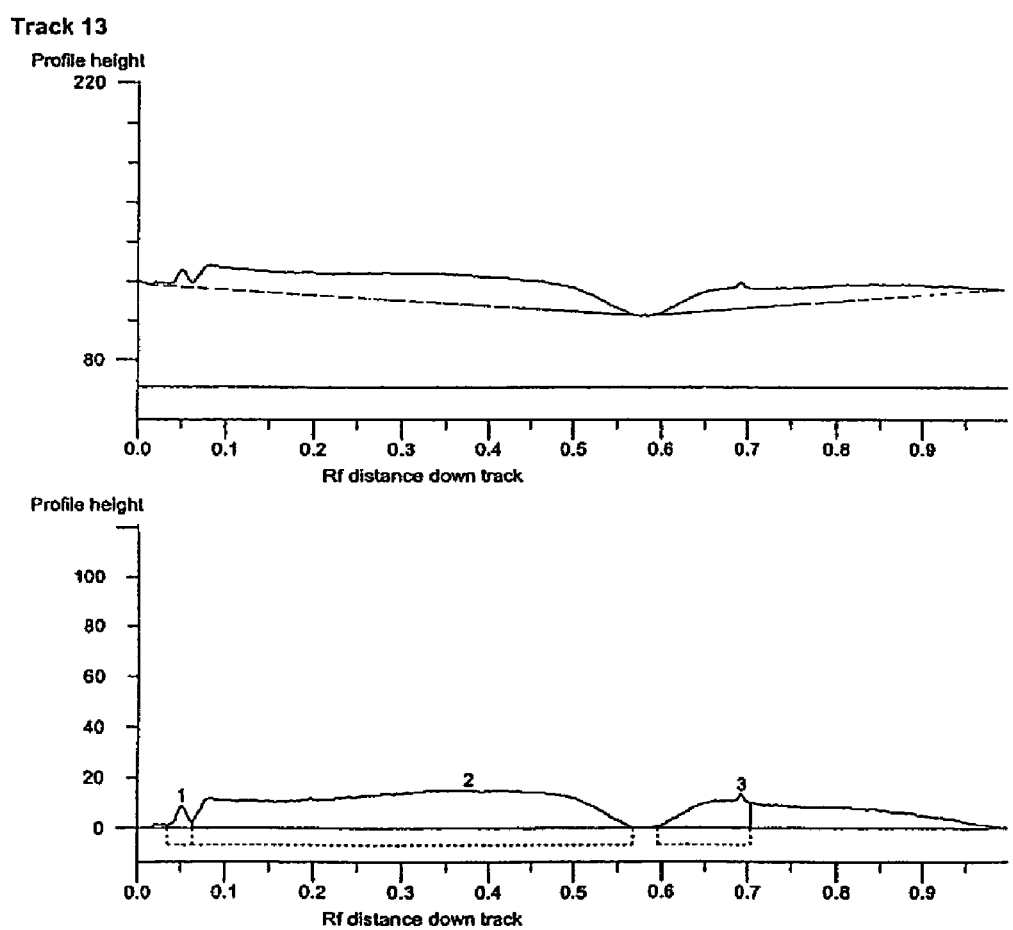
FIG. 17 shows the gel chromatograms for lane 13.

FIGS. 15 to 17 shows the chromatograms. The untreated ssDNA has been heat-treated, therefore only one peak appears in FIG. 15 (indicated by arrow). In FIG. 16, it is apparent that using the amount of DNase I according to the Stemmer and Kikuchi papers the peak for untreated ssDNA is somewhat decreased (indicated by arrow) but no distinct peak is visible for the fragmented DNA, only a smear. Using 6 times more enzyme the untreated ssDNA is totally abolished (FIG. 17) and neither here is any visible peak of the fragments.

Mung Bean Nuclease

Single-stranded DNA was digested with Mung bean nuclease (Product No MO250S, New England Biolabs) using an enzyme concentration of either 0.375 U/ml reaction volume and ssDNA at a concentration of 0.007 µg/µl reaction volume. The reaction buffer comprised 50 mM sodium acetate, 30 mM NaCL, 1 mM $ZnSO_4$, at pH 5.0.

The reaction was allowed to proceed at 25° C. for 10 minutes, before being stopped by heat inactivation (95° C. for 5 minutes).

Shows fragmentation using another endonuclease, Mung bean nuclease was determined. Lane 1 is the untreated ssDNA, lane 2 is the same material treated for 10 minutes. Lane 3 is the MW standard.

Results indicate that all DNA was totally fragmented after only 10 minutes digestion with Mung bean nuclease (see lane 2), despite using the enzyme at a concentration lower than that recommended by the manufacturer.

Conclusions and Comments

The above examples show how the fragment sizes can be controlled using exonucleases and altering the reaction conditions, i.e. time, reaction volume, enzyme concentration. The different peaks are visualised using gel image chromatograms.

In contrast, using endonucleases, such as DNase I, gives a reaction which is hard to control. Using conditions as referred in the literature, either using Mg or Mn containing buffers, typically gives a situation when either everything or nothing is fragmented. An experiment using another endonuclease (Mung bean nuclease) confirms these observations.

Example 5

Digestion of Sub-populations of Single-stranded DNA Starting Material with Different Exonucleases In further experiments, the single-stranded DNA starting material was split into two populations, which were then digested using different exonucleases.

Materials and Methods

Plasmids

A tetracycline-deleted variant of plasmid pBR322 was constructed by cleavage with SalI and BamHI (Roche, Basel, Switzerland) Klenow treatment (Amersham Biosciences AB, Uppsala, Sweden) and blunt-end ligation (New England Biolabs, MA, USA). The resulting plasmid was checked for tetracycline sensitivity and is called pBR322dtet.

PBR322stop1 and pBR322stop3 were created by PCR amplification of the tetracycline gene of pBR322 using specific primers (Table 1). Each mutated tetracycline gene was cloned into pBR322.

TABLE 1

Primer sequences pBR322 NheI forward stop:                         SEQ ID NO:5
5'-CACTATGGCGTGCTGCTAGCGCTATATGCGTTGATGCAATTT
CT ATGAGCACCCGTTCT-3' pBR322 EagI reversed:                             SEQ ID NO:6

TABLE 1-continued

Primer sequences

5'- CGTAGCCCAGCGCGTCGGCCGCCATGCCGGCGATAATG-3' pBR322 HindIII forward:                           SEQ ID NO:7
5'- CAGCTTATCATCGATAAGCTTTAATGCGGTAGTTTAT-3' pBR322 SalI reversed stop:                        SEQ ID NO:8
5'-TCTCAAGGGCATCGGTCGACGCTCTCCCTTATGCGACTCCTGC
ATTAGGAATCAGCCCAGTAGTA-3'

PCR

Unless otherwise noted PCR reactions contained 4 µM of each primer, 160 µM dNTP (Roche, Basel, Switzerland), 1× AmpliTaq reaction buffer, 2.5 U AmpliTaq thermostable DNA polymerase (Applied Biosystems, Calif., USA).

FIND PCR 1: 5 or 25 cycles of 94° C. 30 s, 50° C. 45 s, 72° C. 1 minute and then 72° C. for 7 minutes, no external primers were included.

FIND PCR 2: 15, 25 or 50 cycles of 94° C. 30 s, 55° C. 45 s, 72° C. 1 minute and then 72° C. for 7 minutes with external primers included.

Single-stranded DNA Preparation

The gene of interest, i.e. tet-r, was amplified using specific primers, one of the primer was biotinylated. SsDNA from sense and antisense strains was purified using streptavidin-magnetic beads (purchased from either Dynal AS, Oslo, Norway or Miltenyi Biotec, Bergisch Gladbach, Germany) according to manufacturer's recommendations. The ssDNA hereby obtained was further purified either by ethanol precipitation or by using recochip (TaKaRa, Shiga, Japan) according to manufacturers recommendations.

FIND Experiments

The FIND experiments were initiated by digesting DNA with an exonuclease. The DNA was single-stranded (prepared as above) and originated from the tetracycline resistance gene (pBR322stop1 or pBR322stop3, 945 bp). The exonucleases were BAL31 (0.08-1 U/µg DNA, New England Biolabs, Mass., USA), exonuclease I (100 U/µg DNA, New England Biolabs, Mass., USA), T7 gene 6 exonuclease (320 U/µg DNA, USB, Cleveland Ohio, USA) and exonuclease V (12.5 U/µg DNA, USB, Cleveland Ohio, USA). The time for digestion was in the range 2-90 minutes. The digestion reactions were stopped by adding EDTA to a final concentration of 20 mM and/or heat inactivation at 65 or 95° C. for 10 minutes. When EDTA was used to stop the DNA fragmentation the DNA was further purified by phenol/chloroform extraction and ethanol precipitation. The fragments were recombined in a FIND PCR1 reaction for 5 or 25 cycles and the material was amplified in a FIND PCR 2 reaction for 15, 25 or 50 cycles. Finally the full length genes were cloned into pBR322dtet by the use of HindIII and EagI (New England Biolabs, Mass., USA) for functionality evaluation or into pGEM (Promega, Madison, Wis., USA) for sequencing.

Evaluation of Functionality of Tetracycline Clones

The clones introduced into pBR322dtet were transformed into chemical competent TG1 E. coli and plated on LB agar plates containing 1 µg/ml ampicillin. One to two hundred clones were then moved to LB agar plates containing 50 µg/ml tetracycline and the frequency of tetracycline resistant clones could be calculated.

Results

As shown above, higher frequencies of recombination using the FIND procedure of the present invention could be achieved using ssDNA in the fragmentation. The exonuclease BAL 31 is predominately a 3' exonuclease that removes mononucleotides from both 3' termini of the two strands of a linear double stranded DNA. However BAL 31 can also degrade the single-stranded DNA ends generated by the 3' exonuclease activity on the double stranded DNA. The activity of BAL 31 on ssDNA is removal of mononucleotides from the 5' termini only. Using BAL 31 for fragmentation of ssDNA and then reassembly to full length genes will theoretically result in one cross-over per gene. Experiments were therefore performed to test different exonucleases for the fragmentation of ssDNA. Exonuclease I has 3' activity only whereas BAL 31, T7gene6 and RecJ exonucleases have 5' activity only. Exonuclease V and Exonuclease VII have activity from both ends (5' and 3'). In order to show that these exonucleases can be used in the fragmentation step in a FIND experiment and yield functionally recombined genes a model system based on tetracycline resistance genes was used.

It was found that BAL 31 (FIG. 18a) as well as Exonuclease I (FIG. 18b) and T7 gene 6 exonuclease (FIG. 18c) all worked well in the FIND procedure and a dependency on fragmentation time of recombination frequency was observed.

Figure 18:
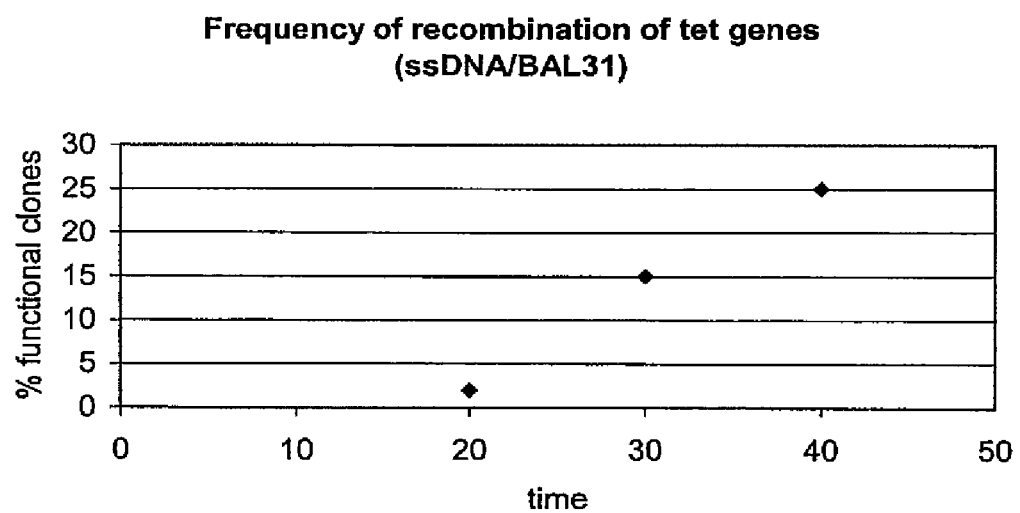
FIG. 18 shows the effect of duration of fragmentation on frequency of recombination of tet-resistance genes following fragmentation of single-stranded DNA with (a) BAL 31, (b) Exo I, (c) T7gene6 and (d) Exo V combined with Exo I.
Figure 18:
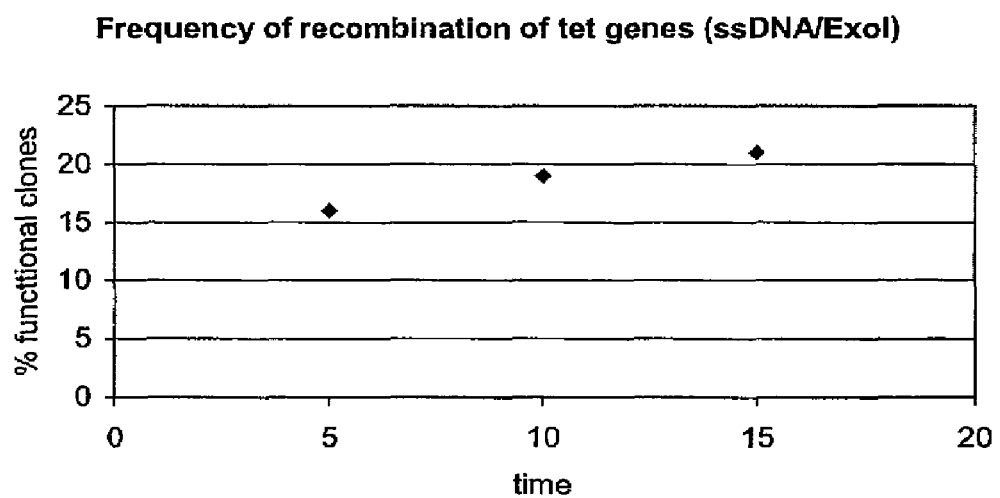
Figure 18:
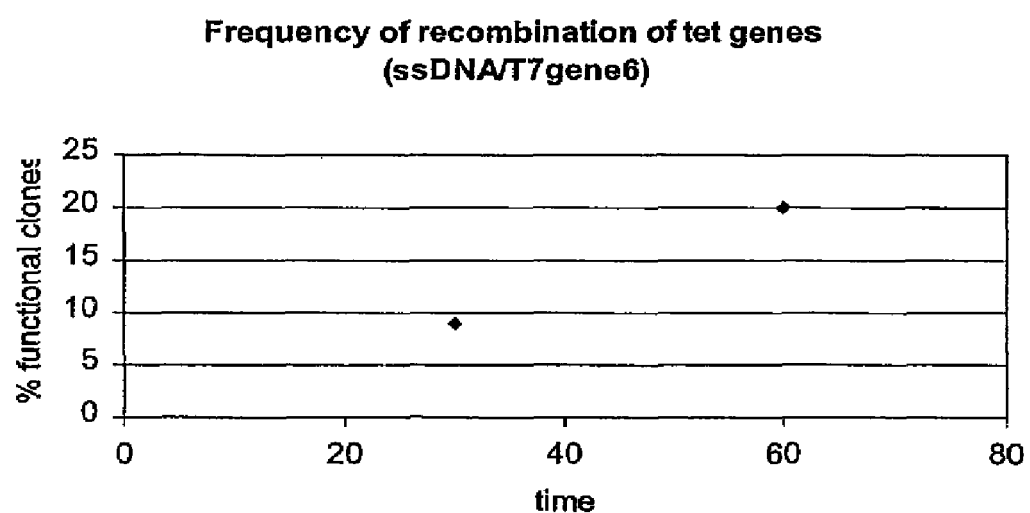
Figure 18:
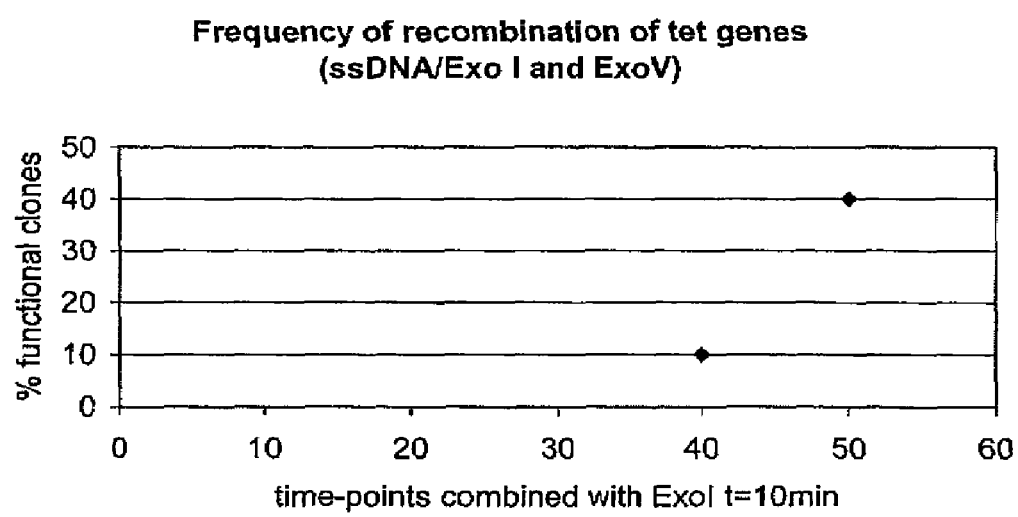

If only one exonuclease, which digests ssDNA from only one end, is used only one cross-over can in theory be achieved. However, it was found that further cross-overs can be obtained if DNA fragments from treatment by different exonucleases were combined. Exonuclease V and Exonuclease VII treatment will result in small fragments without the 5' and 3' ends. These ends are necessary in order to amplify the recombined material in the last PCR reaction. These DNA fragments can therefore be combined with DNA digested from 5' or 3' ends. The result from such a combination can be seen in FIG. 18d where ssDNA treated with Exonuclease I for 10 minutes was combined with ssDNA treated with Exonuclease V for 40 and 50 minutes. Functional clones of up to 40% were obtained, a result that should be compared to the maximum 25% achieved in the same system using only one enzyme (FIG. 18a-c). Fragments have also combined from Exonuclease I and Exonuclease VII treatment, and fragments from T7 gene 6 exonuclease and Exonuclease VII treatment, at different time points, and functionally recombined clones could be obtained (data not shown).

Example 6

Digestion of Sub-populations of Single-stranded DNA Starting Material with Different Exonucleases (Further Experiments)

In a separate set of experiments, multiple cross-overs were produced by combining fragments obtained by digesting single-stranded DNA with Exonuclease I with fragment obtained by digesting single-stranded DNA Exonuclease V and/or Exonuclease VII.

Exonuclease I (Exo I) has only 3' activity whereas Exonuclease V (ExoV) and Exonuclease VII (ExoVII) have activity from both ends (5' and 3'). Hence, ExoV and ExoVII treatment will result in small fragments without the 5' and 3' ends. These ends are necessary in order to amplify the recombined material in the last PCR reaction. These DNA fragments can therefore be combined with DNA digested from 5' or 3' ends only.

Figure 19A:
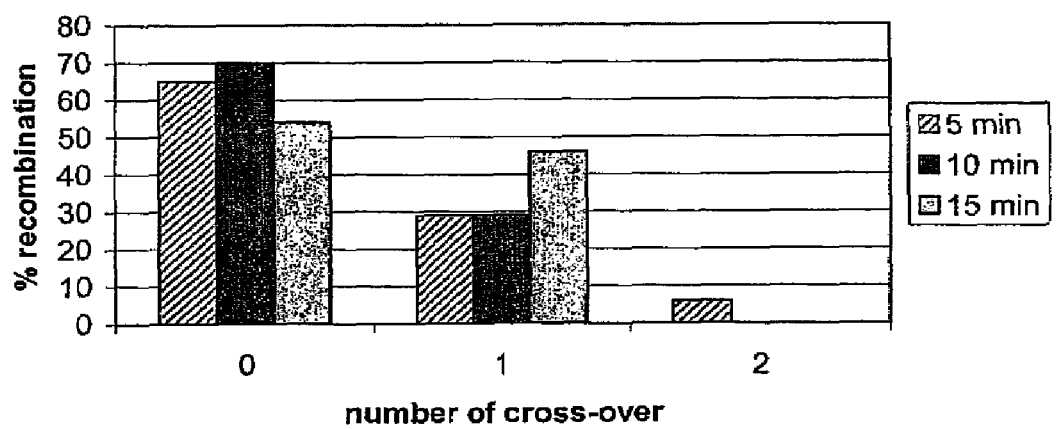
FIG. 19 shows the percentage of multiple cross-overs generated after treatment with different Exonucleases. Frequency of recombination was evaluated for a) ExoI treated ssDNA, b) ExoI (10 min) treated ssDNA combined with ExoVII treated DNA, c) ExoI (10 min) treated ssDNA combined with ExoV treated ssDNA, and d) ExoI (10 min) treated ssDNA combined with ExoV and ExoVII treated ssDNA.
Figure 19:
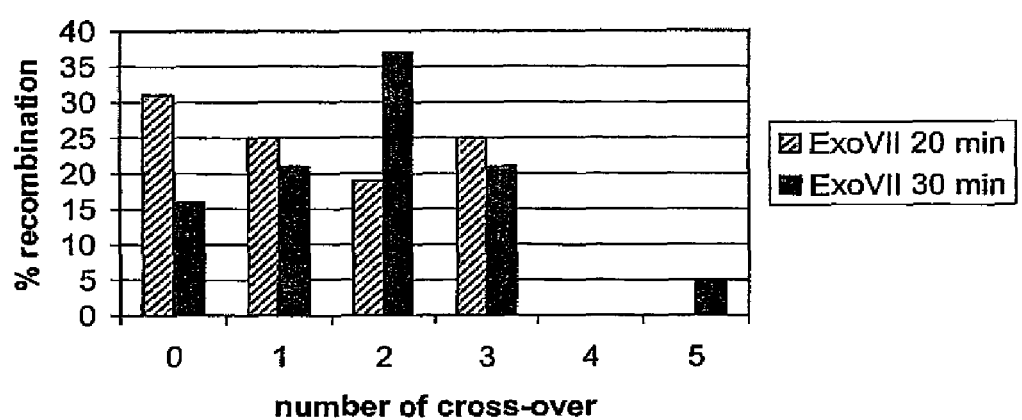
Figure 19:
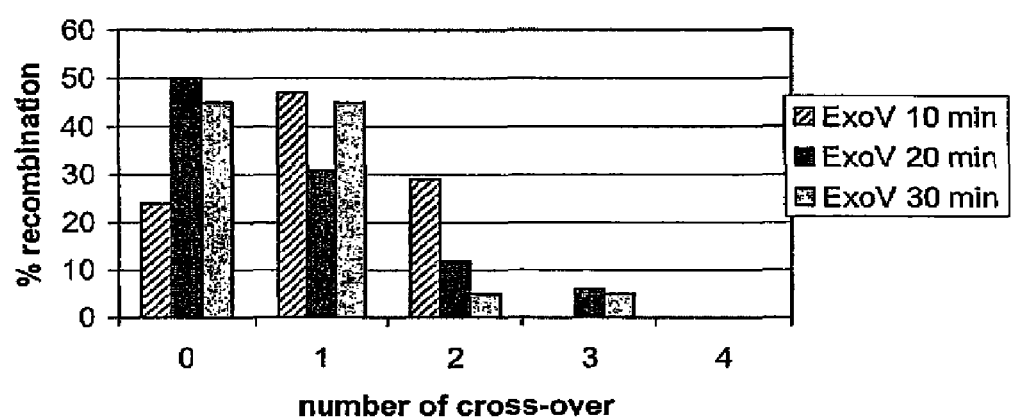
Figure 19:
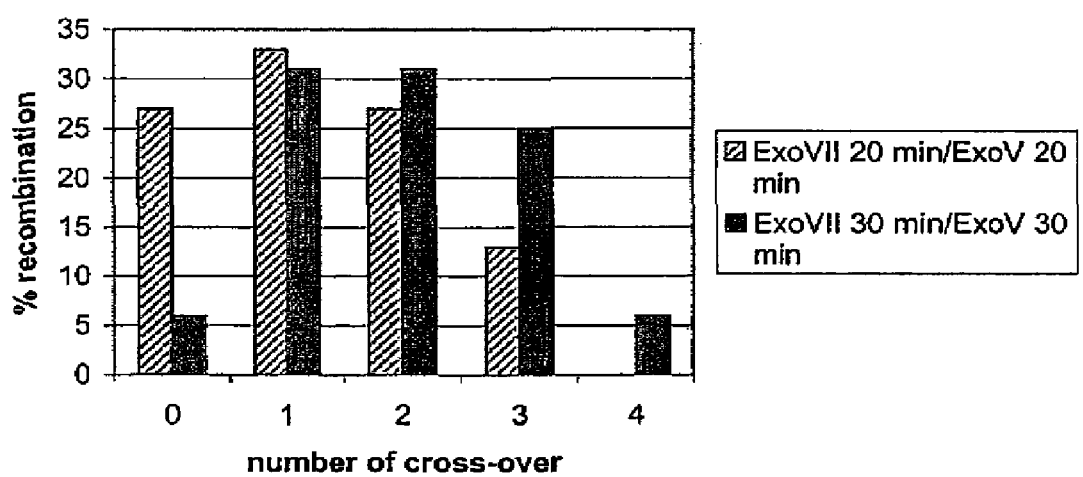

An equimolar mixture of the three scFv genes was used in fragmentation with ExoI, ExoV and ExoVII. Different combination of fragmented material was mixed and PCR reassembled into full length genes and finally sequenced (FIG. 19a-d). ExoI behaved similar to BAL 31 with up to 40% clones with one recombination (FIG. 20a). The combination of ExoI with ExoV or ExoVII increased number of crossover up to five recombinations (FIG. 19 a and c, respectively). ExoVII seems to be more efficient than ExoV, the ExoI/ExoVII combination generated recombinations in over 75% of the clones. Finally, a combination of fragmented DNA from all three enzymes was mixed which generated recombinations (1 to 4) in almost all clones, only 7% of them were wild type genes. Furthermore, longer fragmentation times were most efficient (FIG. 19d). In this particular case the scFv genes consist of large areas of complete homology (the frame work regions), meaning that the number of recombinations identified (up to 4) are the ones that are possible to identify, i.e. the actual number of recombinations might be much higher.

Example 7

Figure 20:
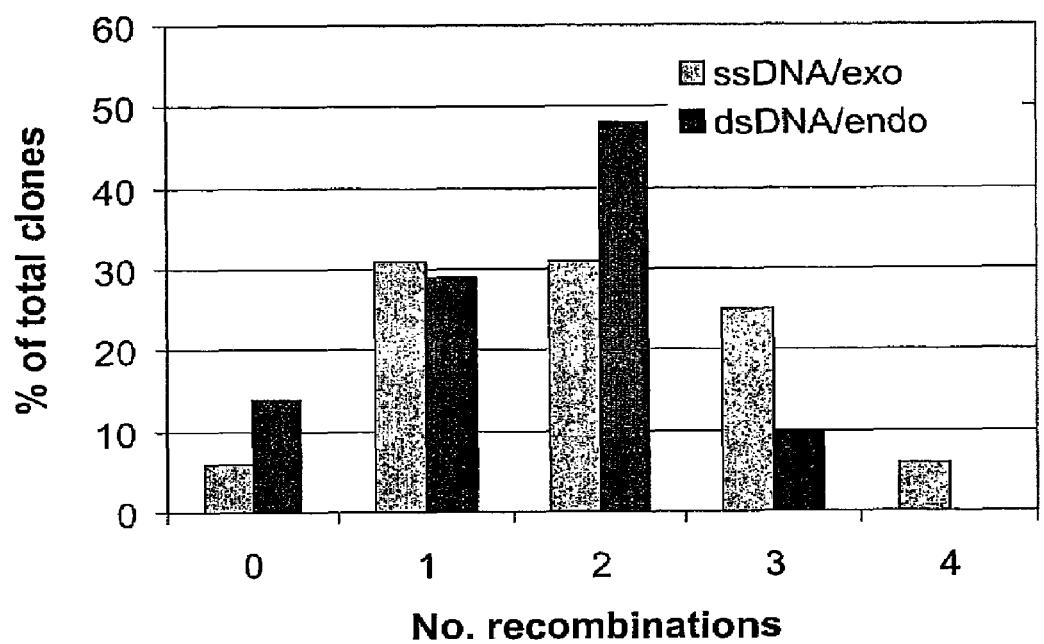
FIG. 20 shows a comparison of the number of recombinations observed following fragmentation of ssDNA with an exonuclease and fragmentation of dsDNA with an endonuclease.

Comparison of the Effects of Digestion of ss DNA with an Exonuclease with the Effects of Digestion of ds DNA with an Endonuclease The experiments in FIG. 20 were carried out by recombining genes coding for three different scFv's using either ssDNA and exonuclease treatment or dsDNA and endonuclease treatment.

Endonuclease digestion of dsDNA was performed using DNase I, as described in Stemmer et al., 1994, *Nature* 370:389-91. Exonuclease digestion of ssDNA was performed using ExoI, ExoV and ExoVII, with equimolar mixes of fragments from ExoI (10 minutes reaction time), ExoV (30 minutes reaction time) and ExoVII (30 minutes reaction time) being used in recombination reactions.

The number of recombinations were evaluated by the use of sequencing. The result shows that ssDNA/exonuclease digestion yields fewer wild type clones and more recombinations.

The invention claimed is:

1. A method for generating a polynucleotide sequence or population of sequences from parent single-stranded polynucleotide sequences encoding one or more protein motifs, the method comprising the steps of
   a) providing a first population of single-stranded polynucleotide molecules and a second population of single-stranded polynucleotide molecules, the first and second populations together constituting plus and minus strands of parent polynucleotide sequences;
   b) carrying out a reaction for digesting the first and second populations of single-stranded polynucleotide molecules with an exonuclease to generate corresponding populations of single-stranded polynucleotide fragments;
   c) contacting said polynucleotide fragments generated from the plus strands with fragments generated from the minus strands; and
   d) amplifying the fragments that anneal to each other to generate at least one polynucleotide sequence encoding one or more protein motifs having altered characteristics as compared to the one or more protein motifs encoded by said parent polynucleotides;
wherein, in step (b), at least one parameter of the reaction used for digestion of the first population of single-stranded polynucleotide molecules is different from the equivalent parameter(s) used in the reaction for digestion of the second population of single-stranded polynucleotide molecules.

2. A method according to claim 1 wherein the reaction parameter is selected from exonuclease type, exonuclease concentration, reaction volume, duration of the digestion reaction, temperature of the reaction mixture, pH of the reaction mixture, length of parent single-stranded polynucleotide sequences, the amount of single-stranded polynucleotide molecules and the buffer composition of the reaction mixture.

3. A method according to claim 1 wherein the exonuclease used for digestion of the first population of single-stranded polynucleotide molecules is different from the exonuclease used for digestion of the second population of single-stranded polynucleotide molecules.

4. A method according to claim 3 wherein the exonuclease used for digestion of the first population of single-stranded polynucleotide molecules is a 3' exonuclease and the exonuclease used for digestion of the second population of single-stranded polynucleotide molecules is a 5' exonuclease.

5. A method according to claim 1 wherein the exonuclease concentration used for digestion of the first population of single-stranded polynucleotide molecules is different from the exonuclease concentration used for digestion of the second population of single-stranded polynucleotide molecules.

6. A method according to claim 1 wherein the reaction volume used for digestion of the first population of single-stranded polynucleotide molecules is different from the reaction volume used for digestion of the second population of single-stranded polynucleotide molecules.

7. A method according to claim 1 wherein the duration of the digestion reaction used for digestion of the first population of single-stranded polynucleotide molecules is different from the duration of the digestion reaction used for digestion of the second population of single-stranded polynucleotide molecules.

8. A method according to claim 1 wherein the temperature of the reaction mixture used for digestion of the first population of single-stranded polynucleotide molecules is different from the temperature of the reaction mixture used for digestion of the second population of single-stranded polynucleotide molecules.

9. A method according to claim 1 wherein the pH of the reaction mixture used for digestion of the first population of single-stranded polynucleotide molecules is different from the pH of the reaction mixture used for digestion of the second population of single-stranded polynucleotide molecules.

10. A method according to claim 1 wherein the length of the polynucleotides in the first population of single-stranded polynucleotide molecules is different from the length of the polynucleotides in the second population of single-stranded polynucleotide molecules.

11. A method according to claim 1 wherein the buffer composition of the reaction mixture used for digestion of the first population of single-stranded polynucleotide molecules is different from the buffer composition of the reaction mixture used for digestion of the second population of single-stranded polynucleotide molecules.

12. A method according to claim 1 wherein the amount of single-stranded polynucleotide molecules in the first population of single-stranded polynucleotide molecules is different from the amount of single-stranded polynucleotide molecules in the second population of single-stranded polynucleotide molecules.

13. A method according to claim 1 wherein the first population of single-stranded polynucleotide molecules constitutes the plus strands of parent polynucleotide sequences and the second population of single-stranded polynucleotide molecules constitutes the minus strands of parent polynucleotide sequences.

14. A method according to claim 1 wherein the polynucleotide molecules of step (a) are DNA molecules.

15. A method according to claim 1 wherein step c) further comprises adding primer sequences that anneal to the 3' and/or 5' ends of at least one of the parent polynucleotides under annealing conditions.

16. A method according to claim 1 wherein the exonuclease used to digest the first and/or second population of single-stranded polynucleotide molecules is selected from the group consisting of BAL 31, exonuclease I, exonuclease V, exonuclease VII, exonuclease T7 gene 6, bacteriophage lambda exonuclease and exonuclease Rec $J_f$.

17. A method according to claim 1 wherein a parent polynucleotide sequence or sequences has been subjected to mutagenesis.

18. A method according to claim 1 wherein one or both of the populations of fragments generated in step b) are subjected to mutagenesis.

19. A method according to claim 1 wherein a parent polynucleotide sequence or sequences has been subjected to mutagenesis using error prone PCR.

20. A method according to claim 1 wherein step b) is carried out to generate populations of single-stranded fragments of varying lengths.

21. A method according to claim 20 wherein step b) is controlled to generate a population of single-stranded fragments having an average length of more than 50 nucleotides.

22. A method according to claim 1 further comprising the step of expressing at least one polynucleotide sequence generated in step d) to produce the encoded polypeptide.

23. A method according to claim 22 further comprising the step of testing the encoded polypeptide for desired characteristics.

24. A method according to claim 1 wherein the parent polynucleotide sequences encode an antibody or fragment thereof.

25. A method according to claim 1 wherein the parent polynucleotide sequences encode an enzyme.

26. A method according to claim 1 wherein the parent polynucleotide sequences encode an antigen.

27. A method for making a polypeptide having desired properties, the method comprising the following steps:
   (a) generating variant forms of a parent polynucleotide using a method according to claim 1;
   (b) expressing the variant polynucleotides produced in step (a) to produce variant polypeptides;
   (c) screening the variant polypeptides for desired properties; and
   (d) selecting a polypeptide having desired properties from the variant polypeptides.

28. A process for preparing a pharmaceutical composition which comprises, following the identification of a polynucleotide and/or encoded polypeptide with desired characteristics by a method according to claim 1, adding said polynucleotide and/or encoded polypeptide to a pharmaceutically acceptable carrier.

29. A process which comprises, following identification of a polynucleotide with desired characteristics according to the method of claim 1, the use of that polynucleotide in the detection and/or amplification of a target polynucleotide in a sample.

* * * * *